United States Patent
Sievers et al.

(10) Patent No.: US 10,722,549 B2
(45) Date of Patent: *Jul. 28, 2020

(54) WEEKLY DOSING REGIMENS FOR ANTI-CD30 VC-PAB-MMAE ANTIBODY DRUG-CONJUGATES

(71) Applicant: SEATTLE GENETICS, INC., Bothell, WA (US)

(72) Inventors: Eric Sievers, Bothell, WA (US); Dana Kennedy, Bothell, WA (US)

(73) Assignee: SEATTLE GENETICS, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/595,430

(22) Filed: Oct. 7, 2019

(65) Prior Publication Data

US 2020/0030405 A1 Jan. 30, 2020

Related U.S. Application Data

(63) Continuation of application No. 16/375,745, filed on Apr. 4, 2019, now Pat. No. 10,478,469, which is a continuation of application No. 16/128,363, filed on Sep. 11, 2018, which is a continuation of application No. 15/622,496, filed on Jun. 14, 2017, now Pat. No. 10,098,963, which is a continuation of application No. 14/938,658, filed on Nov. 11, 2015, now Pat. No. 9,713,648, which is a continuation of application No. 13/143,338, filed as application No. PCT/US2010/020504 on Jan. 8, 2010, now Pat. No. 9,211,319.

(Continued)

(51) Int. Cl.

| | |
|---|---|
| *A61K 38/05* | (2006.01) |
| *A61K 39/00* | (2006.01) |
| *A61K 47/68* | (2017.01) |
| *C07K 16/28* | (2006.01) |
| *C07K 16/30* | (2006.01) |
| *A61K 47/64* | (2017.01) |

(52) U.S. Cl.
CPC .............. *A61K 38/05* (2013.01); *A61K 39/00* (2013.01); *A61K 47/64* (2017.08); *A61K 47/6803* (2017.08); *A61K 47/6811* (2017.08); *A61K 47/6849* (2017.08); *A61K 47/6867* (2017.08); *A61K 47/6889* (2017.08); *C07K 16/2878* (2013.01); *C07K 16/3061* (2013.01); *A61K 2039/505* (2013.01); *C07K 2317/56* (2013.01); *C07K 2317/565* (2013.01); *C07K 2317/77* (2013.01)

(58) Field of Classification Search
CPC ...................................................... A61K 38/05
USPC ....................................................... 424/181.1
See application file for complete search history.

(56) References Cited

U.S. PATENT DOCUMENTS 7,090,843 B1    8/2006 Francisco et al.

7,521,541 B2    4/2009 Eigenbrot et al.
(Continued)

FOREIGN PATENT DOCUMENTS

| WO | WO 05/001038 A2 | 1/2005 |
| WO | WO 2005/084390 A2 | 9/2005 |

(Continued)

OTHER PUBLICATIONS

"Seattle Genetics Reports Multiple Complete and Partial Responses with SGN-35 in Patients with Lymphoma," Drugs.com, 3 pages, (2008). [Retrieved from the Internet Mar. 26, 2015: <URL: http://www.drugs.com/clinical_trials/seattle-genetics-reports-multiple-complete-partial-responses-sgn-35-patients-lymphoma-4630.html>]. [Author Unknown].

(Continued)

*Primary Examiner* — Sean E Aeder
(74) *Attorney, Agent, or Firm* — Alston & Bird LLP

(57) ABSTRACT

Methods for the treatment of CD30-expressing cancers are provided. The methods comprise administering to a subject in need thereof a weekly dose of from about 0.8 mg/kg to about 1.8 mg/kg of an antibody-drug conjugate compound having formula (I); or a pharmaceutically acceptable salt thereof; wherein: mAb is an anti-CD30 antibody unit, S is a sulfur atom of the antibody, A- is a Stretcher unit, and p is from about 3 to about 5.

23 Claims, 2 Drawing Sheets

Specification includes a Sequence Listing.

Related U.S. Application Data

(60) Provisional application No. 61/143,713, filed on Jan. 9, 2009, provisional application No. 61/152,205, filed on Feb. 12, 2009, provisional application No. 61/175,719, filed on May 5, 2009, provisional application No. 61/264,222, filed on Nov. 24, 2009.

(56) References Cited

U.S. PATENT DOCUMENTS

| | | | |
|---|---|---|---|
| 7,619,069 | B2 | 11/2009 | Davies et al. |
| 7,659,241 | B2 | 2/2010 | Senter et al. |
| 7,745,394 | B2 | 6/2010 | Doronina et al. |
| 7,829,531 | B2 | 11/2010 | Senter et al. |
| 8,263,083 | B2 | 9/2012 | Oflazoglu et al. |
| 8,470,329 | B2 | 6/2013 | Oflazoglu et al. |
| 9,211,319 | B2 | 12/2015 | Sievers et al. |
| 9,713,648 | B2 | 7/2017 | Sievers et al. |
| 10,098,963 | B2 | 10/2018 | Sievers et al. |
| 2007/0031402 | A1 | 2/2007 | Zhang et al. |
| 2007/0166309 | A1 | 7/2007 | Lazar et al. |
| 2008/0305044 | A1 | 12/2008 | McDonagh et al. |
| 2018/0369317 | A1 | 12/2018 | Sievers et al. |
| 2019/0224268 | A1 | 7/2019 | Sievers et al. |

FOREIGN PATENT DOCUMENTS

| | | |
|---|---|---|
| WO | WO 06/065533 A2 | 6/2006 |
| WO | WO 09/048967 A1 | 4/2009 |
| WO | WO 10/081004 A1 | 7/2010 |

OTHER PUBLICATIONS

"SGN-35: Antibody-Drug Conjugate," Seattle Genetics, presented at JP Morgan Annual Health Care Conference Jan. 7, 2008.

Anas Younes et al., A Novel Antibody-Drug Conjugate, SGN-35 (Anti-CD30-Auristatin), Induced Objective Responses in Patients with Relapsed or Refractory Hodgkin Lymphoma Preliminary Results of a Phase I Tolerability Study, 7th International Symposium on Hodgkin Lymphoma, Cologne, Nov. 4-7, 2007, poster, 1 page.

Anas Younes, et al., Brentuximab Vedotin (SGN-35) for Relapsed CD30-Postive Lymphomas, Abstract, The New England Journal of Medicine 363;19, Original Article, Nov. 4, 2010, pp. 1812-1821.

Bartlett et al., "Complete remissions with weekly dosing of SGN-35, a novel antibody-drug conjugate (ADC) targeting CD30, in a phase I dose-escalation study in patients with relapsed or refractory Hodgkin lymphoma (HL) or systemic anaplastic large cell lymphoma (sALCL).," J Clin Oncol, 27:15s, (suppl; abstr 8500), (2009).

Bartlett et al., "A Phase I multidose study of SGN-30 immunotherapy in patients with refractory or recurrent CD30 hematologic malignancies," Blood, 111:1848-1854, (2008).

ClinicalTrials.gov Id: NCT00649584, "A Phase I Dose Escalation Study of SGN-35 Alone and in Combination With Gemcitabine for CD30-Positive Malignancies," U.S. National Institutes of Health, Mar. 27, 2008. [Retrieved from the Internet Jul. 12, 2011: <URL: http://clinicaltrials.gov/ct2/show/NCT00649584?term=sgn-35+gemcitabine&rank=1>].

Doronina et al., "Development of potent monoclonalantibody auristatin conjugates for cancer therapy," Nature Biotechnol, 21(7):778-784, (2003). Errata 21:(8):941-941, (2003).

Doronina et al., "Novel Peptide Linkers for Highly Potent Antibody-Auristatin Conjugate," Bioconjugate Chemistry, 19:1960-1963, (2008).

Forero et al., "Initial phase II results of SGN-30 (anti-CD30 monoclonal antibody) in patients ith refractory or recurrent systemic anaplastic large cell lymphoma (ALCL)," Journal of Clinical Oncology, 23:6601, (2005).

Francisco, et al., "cAC10-vcMMAE, an anti-CD30--monomethyl auristatin E conjugate with potent and selective antitumor activity," Blood, 102(4):1458-1465, (2003).

Hamblett et al., "Effects of Drug Loading on the Antitumor Activity of a Monoclonal Antibody Drug Conjugate," Clin Cancer Res, 10:7063-7070, (2004).

Hamblett et al., "SGN-35, an Anti-CD30 Antibody-Drug Conjugate, Exhibits Potent Antitumor Activity for the Treatment of CD30+ Malignancies," Blood, 106:610, (2005).

Holden et al., "A Phase I Study of Weekly Dosing of Trastuzumab-DM1 (T-DM1) in Patients with Advanced HER2+ Breast Cancer," ASCO, Poster, (2008).

Jean-François Haeuw et al., Immunoconjugates, drug-armed antibodies to fight against cancer, Abstract, © 2009 medecin/sciences—Inserm/SRMS, http://www.medecinesciences.org/articles/medsci/abs/2009/12/medsci20092512p1046/me . . . , printed Aug. 19, 2014, 1 page.

Kate Traynor, Pharmacy News: Gemtuzumab Withdrawn From U.S. Market, http://www.ashp.org/menu/News/PharmacyNews/NewsArticle.aspx?id=3358, 2 pages.

Michelle Fanale et al., The Antibody-Drug Conjugate Brentuximab Vedotin (SGN-35) Induced Multiple Objective Responses in Patients with Relapsed Refractory DC30-Postive Lymphomas in a Phase 1 Weekly Dosing Study, Abstract No. 2731, 51st ASH Annual Meeting, Dec. 5-8, 2009, poster, 1 page.

Mylotarg® (gemtuzumab orogamicin for injection), W10477C009 ET01 Rev 08/05, 20 pages.

Oflazoglu, et al., "Combination of the anti-CD30-auristatin-E antibody-drug conjugate (5GN-35) with chemotherapy improves antitumour activity in Hodgkin lymphoma," British Journal of Haematology, 142:69-73, (2008).

Okeley et al., "Specific Tumor Targeting and Potent Bystander Killing with SGN-35, an Anti-CD30 Antibody Drug Conjugate," Blood (ASH Annual Meeting Abstracts), ISSN: 0006-4971, 108(11):Abstract 231, 2006. [Abstract only].

Pinter-Brown, "SGN-30: a basis for the effective treatment of CD30 positive hematopoietic malignancies," Expert Opinion on Investigational Drugs, 17(12):1883-1887, (2008).

Sanderson et al., "In vivo Drug-Linker Stability of an Anti-CD30 Dipeptide-Linked Auristatin Immunoconjugate," Clinical Cancer Research, 11:843-852, (2005). [Retrieved from the Internet May 1, 2017: <http://clincancerres.aacrjournals.org/content/11/2/843.

Seattle Genetics Reports Positive Data from Phase I Weekly-Dosing Clinical Trial of Brentuximab Vedotin (SGN-35) in Lymphoma, Business Wire, Dec. 7, 2009. [Retrieved from the Internet Jul. 12, 2011: <URL: http://investor.seagen.com/phoenix.zhtml?c=124860&p=irol-newsArticle&ID=1362467&highlight= >].

Wahl et al., "The Anti-CD30 Monoclonal Antibody SGN-30 Promotes Growth Arrest and DNA Fragmentation in Vitro and Affects Antitumor Activity in Models of Hodgkin's Disease," Cancer Research, 62:3736-3742, (2002).

Younee et al., "Objective Responses in a Phase I Dose-Escalation Study of SGN-35, a Novel Antibody-Drug Conjugate (ADC) Targeting DC3O, in Patients with Relapsed or Refractory Hodgkin Lymphoma," ASCO, Poster, Abstract No. 8526 (2008).

Younes, et al., "Multiple Complete Responses in a Phase 1 Dose-Escalation Study of the Antibody-Drug Conjugate SGN-35 in Patients with Relapsed or Refractory CD3O-Positive Lymphomas," Blood (ASH Annual Meeting Abstracts), ISSN: 0006-4971, 112:Abstract 1006, (2008). [Abstract only].

EPO Application No. EP 10729571.9, Supplementary European Search Report and European Search Opinion, dated Apr. 20, 2015.

PCT Application No. PCT/US10/20504, International Preliminary Report on Patentability dated Jul. 21, 2011.

PCT Application No. PCT/US10/20504, International Search Report dated Mar. 9, 2010.

PCT Application No. PCT/US10/20504, Written Opinion of the International Searching Authority dated Mar. 9, 2010.

U.S. Appl. No. 13/143,338, Advisory Action dated Feb. 5, 2015.
U.S. Appl. No. 13/143,338, Advisory Action dated Mar. 6, 2015.
U.S. Appl. No. 13/143,338, Final Office Action dated Oct. 24, 2014.
U.S. Appl. No. 13/143,338, Non-Final Office Action dated May 1, 2015.
U.S. Appl. No. 13/143,338, Non-Final Office Action dated Jun. 4, 2014.
U.S. Appl. No. 13/143,338, Notice of Allowance dated Aug. 11, 2015.

(56) References Cited

OTHER PUBLICATIONS

U.S. Appl. No. 14/938,658, Final Office Action dated Mar. 2, 2017.
U.S. Appl. No. 14/938,658, Non-Final Office Action dated May 13, 2016.
U.S. Appl. No. 14/938,658, Non-Final Office Action dated Sep. 23, 2016.
U.S. Appl. No. 14/938,658, Notice of Allowance dated Apr. 5, 2017.
U.S. Appl. No. 14/938,658, Notice of Allowance dated May 18, 2017.
U.S. Appl. No. 15/622,496, Final Office Action and Applicant Initiated Interview Summary dated Mar. 28, 2018.
U.S. Appl. No. 15/622,496, Non-Final Office Action dated Dec. 7, 2017.
U.S. Appl. No. 15/622,496, Notice of Allowance dated Jun. 21, 2018.
U.S. Appl. No. 16/375,745, Non-Final Office Action dated May 21, 2019.
U.S. Appl. No. 16/375,745, Notice of Allowance dated Sep. 19, 2019.
EP Application No. 19159583.4, European Search Report and European Search Opinion dated Aug. 2, 2019.

SEQUENCE LISTING

<160> NUMBER OF SEQ ID NOS: 34

<210> SEQ ID NO 1
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 1

```
cag atc cag ctg cag cag tct gga cct gag gtg gtg aag cct ggg gct      48
Gln Ile Gln Leu Gln Gln Ser Gly Pro Glu Val Val Lys Pro Gly Ala
1               5                   10                  15 tca gtg aag ata tcc tgc aag gct tct ggc tac acc ttc act gac tac      96
Ser Val Lys Ile Ser Cys Lys Ala Ser Gly Tyr Thr Phe Thr Asp Tyr
            20                  25                  30 tat ata acc tgg gtg aag cag aag cct gga cag gga ctt gag tgg att     144
Tyr Ile Thr Trp Val Lys Gln Lys Pro Gly Gln Gly Leu Glu Trp Ile
        35                  40                  45 gga tgg att tat cct gga agc ggt aat act aag tac aat gag aag ttc     192
Gly Trp Ile Tyr Pro Gly Ser Gly Asn Thr Lys Tyr Asn Glu Lys Phe
    50                  55                  60 aag ggc aag gcc aca ttg act gta gac aca tcc tcc agc aca gcc ttc     240
```

```
Lys Gly Lys Ala Thr Leu Thr Val Asp Thr Ser Ser Thr Ala Phe
 65                  70                  75                  80 atg cag ctc agc agc ctg aca tct gag gac act gct gtc tat ttc tgt    288
Met Gln Leu Ser Ser Leu Thr Ser Glu Asp Thr Ala Val Tyr Phe Cys
                 85                  90                  95 gcg aac tat ggt aac tac tgg ttt gct tac tgg ggc caa ggg act cag    336
Ala Asn Tyr Gly Asn Tyr Trp Phe Ala Tyr Trp Gly Gln Gly Thr Gln
                100                 105                 110 gtc act gtc tct gca                                                351
Val Thr Val Ser Ala
            115
```

<210> SEQ ID NO 2
<211> LENGTH: 117
<212> TYPE: PRT
<213> ORGANISM: Mus musculus

<400> SEQUENCE: 2

```
Gln Ile Gln Leu Gln Gln Ser Gly Pro Glu Val Val Lys Pro Gly Ala
 1               5                  10                  15

Ser Val Lys Ile Ser Cys Lys Ala Ser Gly Tyr Thr Phe Thr Asp Tyr
             20                  25                  30

Tyr Ile Thr Trp Val Lys Gln Lys Pro Gly Gln Gly Leu Glu Trp Ile
         35                  40                  45

Gly Trp Ile Tyr Pro Gly Ser Gly Asn Thr Lys Tyr Asn Glu Lys Phe
     50                  55                  60

Lys Gly Lys Ala Thr Leu Thr Val Asp Thr Ser Ser Thr Ala Phe
 65                  70                  75                  80

Met Gln Leu Ser Ser Leu Thr Ser Glu Asp Thr Ala Val Tyr Phe Cys
                 85                  90                  95

Ala Asn Tyr Gly Asn Tyr Trp Phe Ala Tyr Trp Gly Gln Gly Thr Gln
                100                 105                 110

Val Thr Val Ser Ala
            115
```

<210> SEQ ID NO 3
<211> LENGTH: 15
<212> TYPE: DNA
<213> ORGANISM: Mus musculus

<400> SEQUENCE: 3
gactactata taacc                                                   15

<210> SEQ ID NO 4
<211> LENGTH: 5
<212> TYPE: PRT
<213> ORGANISM: Mus musculus

<400> SEQUENCE: 4

```
Asp Tyr Tyr Ile Thr
 1               5
```

<210> SEQ ID NO 5
<211> LENGTH: 51
<212> TYPE: DNA
<213> ORGANISM: Mus musculus

<400> SEQUENCE: 5
tggatttatc ctggaagcgg taatactaag tacaatgaga agttcaaggg c            51

```
<210> SEQ ID NO 6
<211> LENGTH: 17
<212> TYPE: PRT
<213> ORGANISM: Mus musculus

<400> SEQUENCE: 6

Trp Ile Tyr Pro Gly Ser Gly Asn Thr Lys Tyr Asn Glu Lys Phe Lys
1               5                   10                  15

Gly

<210> SEQ ID NO 7
<211> LENGTH: 24
<212> TYPE: DNA
<213> ORGANISM: Mus musculus

<400> SEQUENCE: 7
tatggtaact actggtttgc ttac                                            24

<210> SEQ ID NO 8
<211> LENGTH: 8
<212> TYPE: PRT
<213> ORGANISM: Mus musculus

<400> SEQUENCE: 8

Tyr Gly Asn Tyr Trp Phe Ala Tyr
1               5

<210> SEQ ID NO 9
<211> LENGTH: 333
<212> TYPE: DNA
<213> ORGANISM: Mus musculus
<220> FEATURE:
<221> NAME/KEY: CDS
<222> LOCATION: (1)..(333)

<400> SEQUENCE: 9 gac att gtg ctg acc caa tct cca gct tct ttg gct gtg tct cta ggg        48
Asp Ile Val Leu Thr Gln Ser Pro Ala Ser Leu Ala Val Ser Leu Gly
1               5                   10                  15 cag agg gcc acc atc tcc tgc aag gcc agc caa agt gtt gat ttt gat        96
Gln Arg Ala Thr Ile Ser Cys Lys Ala Ser Gln Ser Val Asp Phe Asp
            20                  25                  30 ggt gat agt tat atg aac tgg tac caa cag aaa cca gga cag cca ccc       144
Gly Asp Ser Tyr Met Asn Trp Tyr Gln Gln Lys Pro Gly Gln Pro Pro
        35                  40                  45 aaa gtc ctc atc tat gct gca tcc aat cta gaa tct ggg atc cca gcc       192
Lys Val Leu Ile Tyr Ala Ala Ser Asn Leu Glu Ser Gly Ile Pro Ala
    50                  55                  60 agg ttt agt ggc agt ggg tct ggg aca gac ttc acc ctc aac atc cat       240
Arg Phe Ser Gly Ser Gly Ser Gly Thr Asp Phe Thr Leu Asn Ile His
65                  70                  75                  80 cct gtg gag gag gag gat gct gca acc tat tac tgt cag caa agt aat       288
Pro Val Glu Glu Glu Asp Ala Ala Thr Tyr Tyr Cys Gln Gln Ser Asn
                85                  90                  95 gag gat ccg tgg acg ttc ggt gga ggc acc aag ctg gaa atc aaa           333
Glu Asp Pro Trp Thr Phe Gly Gly Gly Thr Lys Leu Glu Ile Lys
            100                 105                 110

<210> SEQ ID NO 10
<211> LENGTH: 111
<212> TYPE: PRT
<213> ORGANISM: Mus musculus

<400> SEQUENCE: 10
```

-continued

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Thr Lys Leu Glu Ile Lys
            100                 105                 110

<210> SEQ ID NO 11
<211> LENGTH: 45
<212> TYPE: DNA
<213> ORGANISM: Mus musculus

<400> SEQUENCE: 11
aaggccagcc aaagtgttga ttttgatggt gatagttata tgaac            45

<210> SEQ ID NO 12
<211> LENGTH: 15
<212> TYPE: PRT
<213> ORGANISM: Mus musculus

<400> SEQUENCE: 12

Lys Ala Ser Gln Ser Val Asp Phe Asp Gly Asp Ser Tyr Met Asn
1               5                   10                  15

<210> SEQ ID NO 13
<211> LENGTH: 21
<212> TYPE: DNA
<213> ORGANISM: Mus musculus

<400> SEQUENCE: 13
gctgcatcca atctagaatc t                                      21

<210> SEQ ID NO 14
<211> LENGTH: 7
<212> TYPE: PRT
<213> ORGANISM: Mus musculus

<400> SEQUENCE: 14

Ala Ala Ser Asn Leu Glu Ser
1               5

<210> SEQ ID NO 15
<211> LENGTH: 27
<212> TYPE: DNA
<213> ORGANISM: Mus musculus

<400> SEQUENCE: 15
cagcaaagta atgaggatcc gtggacg                                27

<210> SEQ ID NO 16
<211> LENGTH: 9
<212> TYPE: PRT
<213> ORGANISM: Mus musculus

<400> SEQUENCE: 16

Gln Gln Ser Asn Glu Asp Pro Trp Thr
1               5

<210> SEQ ID NO 17
<211> LENGTH: 375
<212> TYPE: DNA
<213> ORGANISM: Mus musculus
<220> FEATURE:
<221> NAME/KEY: CDS
<222> LOCATION: (1)..(375)

<400> SEQUENCE: 17

```
gag gtg aag ctg gtg gag tct gga gga ggc ttg gta cag cct ggg ggt      48
Glu Val Lys Leu Val Glu Ser Gly Gly Gly Leu Val Gln Pro Gly Gly
1               5                   10                  15 tct ctg aga ctc tcc tgt gca act tct ggg ttc acc ttc agt gat tac      96
Ser Leu Arg Leu Ser Cys Ala Thr Ser Gly Phe Thr Phe Ser Asp Tyr
            20                  25                  30 tat atg aac tgg gtc cgc cag cct cca gga aag gct ctt gag tgg ttg     144
Tyr Met Asn Trp Val Arg Gln Pro Pro Gly Lys Ala Leu Glu Trp Leu
        35                  40                  45 ggt ttt att aga aac aaa gct aat ggt tac aca aca gag ttc agt gca     192
Gly Phe Ile Arg Asn Lys Ala Asn Gly Tyr Thr Thr Glu Phe Ser Ala
    50                  55                  60 tct gtg atg ggt cgg ttc acc atc tcc aga gat gat tcc caa agc atc     240
Ser Val Met Gly Arg Phe Thr Ile Ser Arg Asp Asp Ser Gln Ser Ile
65                  70                  75                  80 ctc tat ctt cag atg aac acc ctg aga gct gag gac agt gcc act tat     288
Leu Tyr Leu Gln Met Asn Thr Leu Arg Ala Glu Asp Ser Ala Thr Tyr
                85                  90                  95 tac tgt gca aga gat ccc ccc tat ggt aac ccc cat tat tat gct atg     336
Tyr Cys Ala Arg Asp Pro Pro Tyr Gly Asn Pro His Tyr Tyr Ala Met
            100                 105                 110 gac tac tgg ggt caa gga acc tca gtc acc gtc tcc tca                 375
Asp Tyr Trp Gly Gln Gly Thr Ser Val Thr Val Ser Ser
        115                 120                 125
```

<210> SEQ ID NO 18
<211> LENGTH: 125
<212> TYPE: PRT
<213> ORGANISM: Mus musculus

<400> SEQUENCE: 18

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Tyr Met Asn Trp Val Arg Gln Pro Pro Gly Lys Ala Leu Glu Trp Leu
        35                  40                  45

Gly Phe Ile Arg Asn Lys Ala Asn Gly Tyr Thr Thr Glu Phe Ser Ala
    50                  55                  60

Ser Val Met Gly Arg Phe Thr Ile Ser Arg Asp Asp Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Pro Pro Tyr Gly Asn Pro His Tyr Tyr Ala Met
            100                 105                 110

Asp Tyr Trp Gly Gln Gly Thr Ser Val Thr Val Ser Ser

<210> SEQ ID NO 19
<211> LENGTH: 15
<212> TYPE: DNA
<213> ORGANISM: Mus musculus

<400> SEQUENCE: 19
gattactata tgaac                                             15

<210> SEQ ID NO 20
<211> LENGTH: 5
<212> TYPE: PRT
<213> ORGANISM: Mus musculus

<400> SEQUENCE: 20

Asp Tyr Tyr Met Asn
1               5

<210> SEQ ID NO 21
<211> LENGTH: 57
<212> TYPE: DNA
<213> ORGANISM: Mus musculus

<400> SEQUENCE: 21
tttattagaa acaaagctaa tggttacaca acagagttca gtgcatctgt gatgggt     57

<210> SEQ ID NO 22
<211> LENGTH: 19
<212> TYPE: PRT
<213> ORGANISM: Mus musculus

<400> SEQUENCE: 22

Phe Ile Arg Asn Lys Ala Asn Gly Tyr Thr Thr Glu Phe Ser Ala Ser
1               5                   10                  15

Val Met Gly

<210> SEQ ID NO 23
<211> LENGTH: 42
<212> TYPE: DNA
<213> ORGANISM: Mus musculus

<400> SEQUENCE: 23 gatccccct atggtaaccc ccattattat gctatggact ac                 42

<210> SEQ ID NO 24
<211> LENGTH: 14
<212> TYPE: PRT
<213> ORGANISM: Mus musculus

<400> SEQUENCE: 24

Asp Pro Pro Tyr Gly Asn Pro His Tyr Tyr Ala Met Asp Tyr
1               5                   10

<210> SEQ ID NO 25
<211> LENGTH: 333
<212> TYPE: DNA
<213> ORGANISM: Mus musculus
<220> FEATURE:
<221> NAME/KEY: CDS
<222> LOCATION: (1)..(333)

<400> SEQUENCE: 25 gac att gtg ctg acc cag tct cct gct tcc tta gct gtt tct ctg ggg    48

```
Asp Ile Val Leu Thr Gln Ser Pro Ala Ser Leu Ala Val Ser Leu Gly
1               5                   10                  15 cag agg gcc acc atc tca tgc agg gcc agc aaa agt gtc agt gca tct        96
Gln Arg Ala Thr Ile Ser Cys Arg Ala Ser Lys Ser Val Ser Ala Ser
                20                  25                  30 ggc tat aat tat atg cac tgg tac caa cag aaa gca ggg cag cca ccc        144
Gly Tyr Asn Tyr Met His Trp Tyr Gln Gln Lys Ala Gly Gln Pro Pro
            35                  40                  45 aaa ctc ctc atc cat ctt gca tcc aac cta gaa tct ggg gtc cct gcc        192
Lys Leu Leu Ile His Leu Ala Ser Asn Leu Glu Ser Gly Val Pro Ala
        50                  55                  60 agg ttc agt ggc agt ggg tct ggg aca gac ttc acc ctc aac atc cat        240
Arg Phe Ser Gly Ser Gly Ser Gly Thr Asp Phe Thr Leu Asn Ile His
65                  70                  75                  80 cct gtg gag gag gag gat gct tca acc tat tac tgt cag cac agt ggg        288
Pro Val Glu Glu Glu Asp Ala Ser Thr Tyr Tyr Cys Gln His Ser Gly
                85                  90                  95 gag ctt cca ttc acg ttc ggc tcg ggg aca aag ttg gaa ata aaa            333
Glu Leu Pro Phe Thr Phe Gly Ser Gly Thr Lys Leu Glu Ile Lys
            100                 105                 110

<210> SEQ ID NO 26
<211> LENGTH: 111
<212> TYPE: PRT
<213> ORGANISM: Mus musculus

<400> SEQUENCE: 26

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ala Ser
                20                  25                  30

Gly Tyr Asn Tyr Met His Trp Tyr Gln Gln Lys Ala Gly Gln Pro Pro
            35                  40                  45

Lys Leu Leu Ile His Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ser Thr Tyr Tyr Cys Gln His Ser Gly
                85                  90                  95

Glu Leu Pro Phe Thr Phe Gly Ser Gly Thr Lys Leu Glu Ile Lys
            100                 105                 110

<210> SEQ ID NO 27
<211> LENGTH: 45
<212> TYPE: DNA
<213> ORGANISM: Mus musculus

<400> SEQUENCE: 27
agggccagca aaagtgtcag tgcatctggc tataattata tgcac                      45

<210> SEQ ID NO 28
<211> LENGTH: 15
<212> TYPE: PRT
<213> ORGANISM: Mus musculus

<400> SEQUENCE: 28

Arg Ala Ser Lys Ser Val Ser Ala Ser Gly Tyr Asn Tyr Met His
1               5                   10                  15

<210> SEQ ID NO 29
```

```
<211> LENGTH: 21
<212> TYPE: DNA
<213> ORGANISM: Mus musculus

<400> SEQUENCE: 29
cttgcatcca acctagaatc t                                              21

<210> SEQ ID NO 30
<211> LENGTH: 7
<212> TYPE: PRT
<213> ORGANISM: Mus musculus

<400> SEQUENCE: 30

Leu Ala Ser Asn Leu Glu Ser
1               5

<210> SEQ ID NO 31
<211> LENGTH: 27
<212> TYPE: DNA
<213> ORGANISM: Mus musculus

<400> SEQUENCE: 31
cagcacagtg gggagcttcc attcacg                                        27

<210> SEQ ID NO 32
<211> LENGTH: 9
<212> TYPE: PRT
<213> ORGANISM: Mus musculus

<400> SEQUENCE: 32

Gln His Ser Gly Glu Leu Pro Phe Thr
1               5

<210> SEQ ID NO 33
<211> LENGTH: 330
<212> TYPE: PRT
<213> ORGANISM: Homo sapiens

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 106
<212> TYPE: PRT
<213> ORGANISM: Homo sapiens

<400> SEQUENCE: 34

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

WEEKLY DOSING REGIMENS FOR ANTI-CD30 VC-PAB-MMAE ANTIBODY DRUG-CONJUGATES

CROSS REFERENCE TO RELATED APPLICATIONS

This application is a continuation of U.S. application Ser. No. 16/375,745 filed Apr. 4, 2019, which is a continuation of U.S. application Ser. No. 16/128,363 filed Sep. 11, 2018, which is a continuation of U.S. application Ser. No. 15/622,496 filed Jun. 14, 2017 now U.S. Pat. No. 10,098,963, which is a continuation of U.S. application Ser. No. 14/938,658 filed Nov. 11, 2015 now U.S. Pat. No. 9,713,648, which is a continuation of U.S. application Ser. No. 13/143,338 filed Jul. 5, 2011 now U.S. Pat. No. 9,211,319, which is a National Stage Entry of International Application No. PCT/US10/20504 filed Jan. 8, 2010, which claims priority from U.S. Provisional Application No. 61/264,222 filed Nov. 24, 2009; U.S. Provisional Application No. 61/175,719 filed May 5, 2009, U.S. Provisional Application No. 61/152,205 filed Feb. 12, 2009, and U.S. Provisional Application No. 61/143,713 filed Jan. 9, 2009, each of which is incorporated by reference in its entirety for all purposes.

REFERENCE TO A SEQUENCE LISTING

This application includes a sequence listing submitted herewith as a text filed named "538559_SEQLIST.txt" created on Oct. 3, 2019 and containing 19,820 byte. The material 7 contained in this text file is incorporated by reference.

FIELD

The present invention relates, inter alia, to methods for the treatment of a CD30-expressing hematologic cancer comprising administering to a subject in need thereof a weekly dose of from about 0.8 mg/kg to about 1.8 mg/kg of an anti-CD30 vc-PAB MMAE antibody-drug conjugate.

BACKGROUND

Hodgkin lymphoma (HL) is a neoplasm of lymphoid tissue that is defined histopathologically by the presence of the malignant Hodgkin-Reed—Sternberg (HRS) cells. The characteristic surface antigen expressed on HRS cells is CD30. There are an estimated 8,000 new HL cases diagnosed annually in the United States and Canada. Advances in the use of combined chemotherapy and radiotherapy in HL over the past half-century have resulted in a durable remission rate of approximately 70%. However, these multi-agent regimens confer a significant morbidity on patients, including secondary malignancies, cardiac disease, and infertility. Furthermore, approximately 30% of patients presenting with HL will become refractory to initial therapy or will relapse. Salvage chemotherapy regimens and autologous stem cell transplant (ASCT) are secondary options for these patients, but both are associated with significant morbidity and limited long term disease control. Patients who relapse after ASCT or are ineligible for salvage therapy have a very poor prognosis. Currently, there is a lack of well-tolerated, efficacious treatment options for these patients. Thus, there continues to be an unmet medical need for patients suffering from HL and other CD30 expressing cancers. The present invention addresses this and other needs.

DETAILED DESCRIPTION OF EXEMPLARY EMBODIMENTS

A. General Introduction

Figure 1:
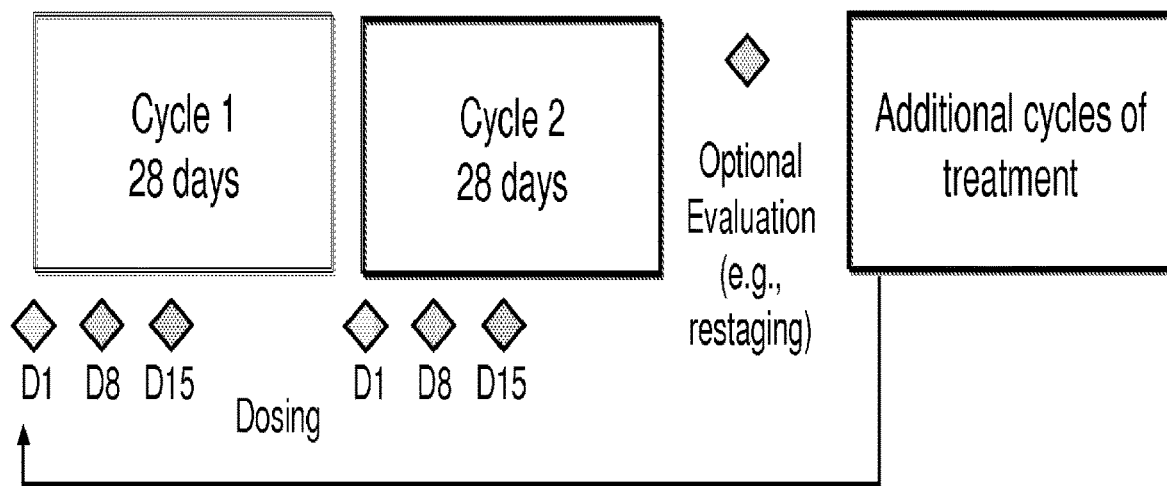
FIG. 1: Exemplary administration schedule for an antibody drug conjugate. The antibody drug conjugate is administered in a single weekly dose, three out of 4 weeks, every 28 days.
Figure 2:
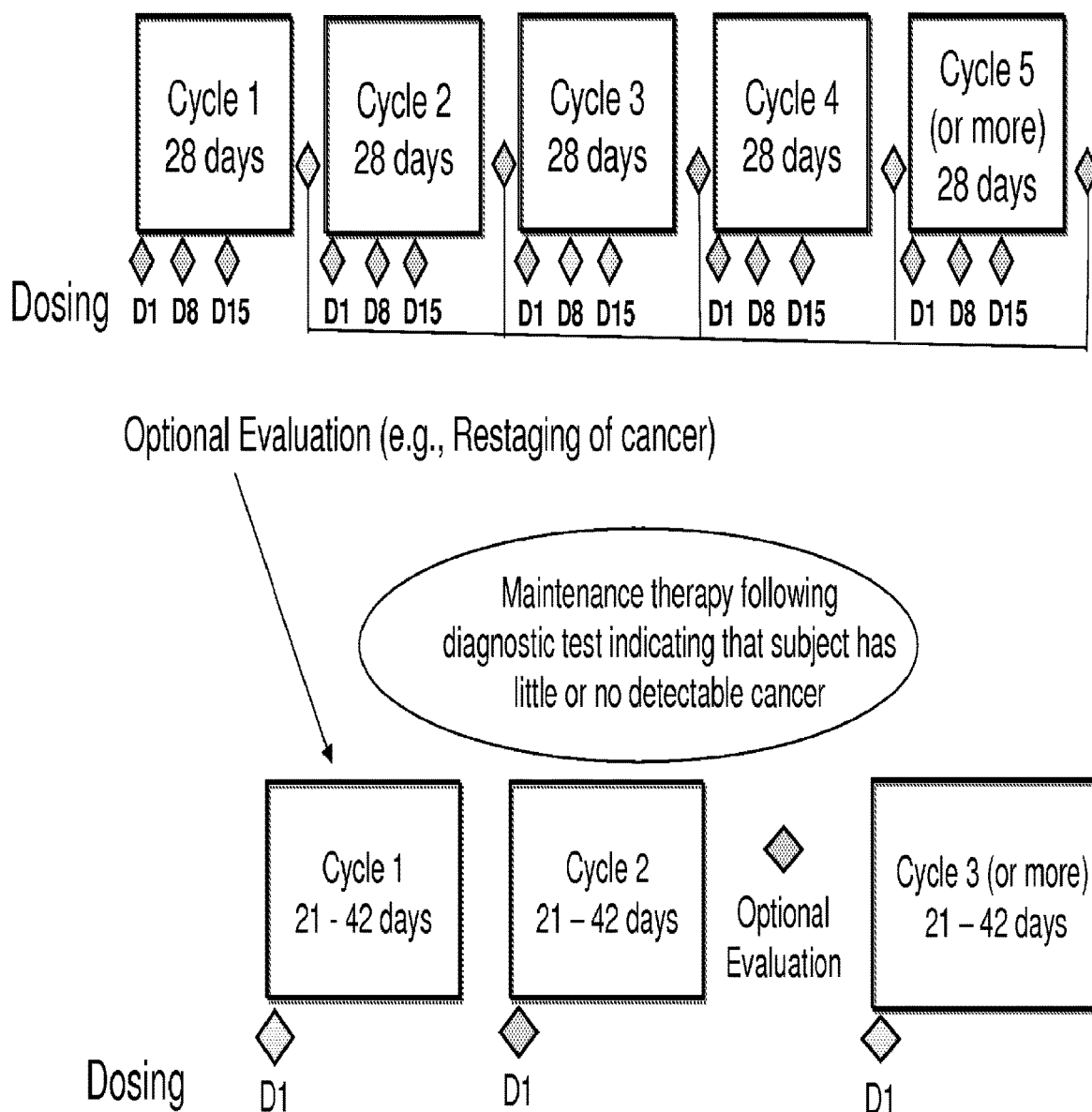
FIG. 2: Exemplary administration schedule for an antibody drug conjugate. The antibody drug conjugate is administered in a single weekly dose, three out of 4 weeks. Following an evaluation indicating that the subject has no detectable signs of cancer, the administration schedule is reduced to once every three to six weeks.

The present invention provides, inter alia, methods for treating a CD30-expressing hematologic cancer. The present inventors have discovered that a weekly therapeutic regimen with the anti-CD30 antibody-drug conjugate cAC10-(MC-vc-PAB-MMAE)$_4$ at doses of about 0.8 mg/kg to about 1.2 mg/kg provides a surprisingly efficacious therapeutic regimen, e.g., it allows for multiple objective responses within a short time period and has an acceptable tolerability profile despite frequent dosing. That such a substantial dose of the antibody-drug conjugate can be provided at such frequent intervals and result in a high response rate and acceptable toxicity profile is a surprising finding. In a phase I study, multiple complete responses were observed within 8 weeks of treatment. The weekly dosing regimen has been observed to provide a high rate of response in a short time period. The high rate of response is also surprising for a drug delivered, not as a combination therapy, but as a monotherapy, for the treatment of cancer. Accordingly, the present methods provide, inter alia, a weekly dosing regimen for administering an anti-CD30 vc-PAB-MMAE antibody-drug conjugate to a subject. In some embodiments, the weekly dosing regimen increases the subject's probability of responding to the therapy as compared to other dosing regimens (e.g., as compared to an every three week dosing regimen). In some embodiments, the dosing regimen does not increase the subject's probability of suffering from an adverse event (including a dose limiting toxicity) as compared to other dosing regimens (e.g., as compared to an every three week dosing regimen) despite the fact that the total dose of antibody drug conjugate over a treatment cycle may be greater for the weekly dosing regimen as compared to other dosing regimens. The present invention also provides, inter alia, maintenance therapy following the weekly dosing regimen.

For clarity of disclosure, and not by way of limitation, the detailed description of the invention is divided into the subsections which follow.

B. Summary

The present invention is based, inter alia, on the discovery that weekly dosing of a cAC10-MC-vc-PAB-MMAE antibody drug conjugate (Sanderson et al., *Clinical Cancer Research* 2005 11:843-852, incorporated by reference herein in its entirety and for all purposes) provides a surprisingly high rate of response with an acceptable tolerability profile.

C. Definitions and Abbreviations

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The term "inhibit" or "inhibition of" as used herein means to a reduce by a measurable amount, or to prevent entirely.

The transitional phrase "consisting essentially of" as used herein limits the scope of a claim to the specified active agents or steps and those additional active agents and steps that do not materially affect the properties of the specified active agents.

The term "agent" as used herein means an element, compound, or molecular entity, including, e.g., a pharmaceutical, therapeutic, or pharmacologic compound. Agents can be natural or synthetic or a combination thereof.

An "anti-cancer agent" is an agent that exerts a cytotoxic or cytostatic effect on cancer cells either alone or in combination with another agent as part of a treatment regimen. An "anti-cancer agent" can slow, stop, or reverse the progression of cancer in a subject. For example, an anti-cancer agent is an agent that can inhibit tumor growth, arrest tumor growth, and/or cause the regression of already existing tumors. Anti-inflammatory agents or other agents administered to a subject with cancer to treat symptoms associated with cancer, but not the underlying cancer itself, including, for example inflammation, pain, weight loss, and general malaise are not considered anti-cancer agents.

"Cytotoxic effect," in reference to the effect of an agent on a cell, means killing of the cell. "Cytostatic effect" means an inhibition of cell proliferation. A "cytotoxic agent" means an agent that has a cytotoxic or cytostatic effect on a cell, thereby depleting or inhibiting the growth of, respectively, cells within a cell population.

The term "deplete," in the context of the effect of an anti-CD30 antibody-drug conjugate on CD30-expressing cells, refers to a reduction or elimination of the CD30-expressing cells.

As used herein, the terms "treatment" or "treat" refer to slowing, stopping, or reversing the progression of a CD30-expressing disease in a subject.

The terms "specific binding" and "specifically binds" mean that the anti-CD30 antibody will react, in a highly selective manner, with its corresponding target, CD30, and not with the multitude of other antigens. Typically, the anti-CD30 antibody binds with an affinity of at least about $1\times10^{-7}$M, and preferably $1\times10^{-8}$ M to $1\times10^{-9}$ M, $1\times10^{-10}$ M, $1\times10^{-11}$ M, or $1\times10^{-12}$ M.

The term "monoclonal antibody" refers to an antibody that is derived from a single cell clone, including any eukaryotic or prokaryotic cell clone, or a phage clone, and not the method by which it is produced. Thus, the term "monoclonal antibody" as used herein is not limited to antibodies produced through hybridoma technology.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In certain embodiments, the two sequences are the same length.

The term "substantially identical," in the context of two nucleic acids or polypeptides, refers to two or more sequences or subsequences that have at least 70% or at least 75% identity; more typically at least 80% or at least 85% identity; and even more typically at least 90%, at least 95%, or at least 98% identity (for example, as determined using one of the methods set forth below).

The determination of percent identity between two sequences can be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul, et al., 1990, *J. Mol. Biol.* 215:403-410. BLAST nucleotide searches can be performed with the NBLAST program, score=100, wordlength=12 to obtain nucleotide sequences homologous to a nucleic acid encoding a protein of interest. BLAST protein searches can be performed with the XBLAST program, score=50, wordlength=3 to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA.

Alternatively, protein sequence alignment may be carried out using the CLUSTAL W algorithm, as described by Higgins et al., 1996, *Methods Enzymol.* 266:383-402.

The term "pharmaceutically acceptable" as used herein refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term "pharmaceutically compatible ingredient" refers to a pharmaceutically acceptable diluent, adjuvant, excipient, or vehicle with which an antibody-drug conjugate is administered.

The abbreviation "MMAE" refers to monomethyl auristatin E.

The abbreviations "vc" and "val-cit" refer to the dipeptide valine-citrulline.

The abbreviation "PAB" refers to the self-immolative spacer:

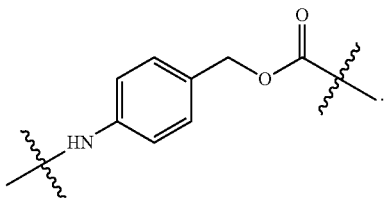 [SMILES: *Nc1ccc(COC(*)=O)cc1]

The abbreviation "MC" refers to the stretcher maleimidocaproyl:

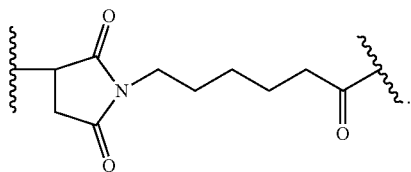 [SMILES: *C(=O)CCCCCN1C(=O)CC(*)C1=O]

cAC10-MC-vc-PAB-MMAE refers to a chimeric AC10 antibody conjugated to the drug MMAE through a MC-vc-PAB linker.

An anti-CD30 vc-PAB-MMAE antibody-drug conjugate refers to an anti-CD30 antibody conjugated to the drug MMAE via a linker comprising the dipeptide valine citrulline and the self-immolative spacer PAB as shown in Formula (I).

The phrase "single weekly dose" as it refers to administration of an antibody-drug conjugate refers to administration of the drug once in a weekly period. In contrast, a "split-delivery dose" during a weekly period refers to administration of the drug more than once during the weekly time period.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Unless otherwise noted, the term "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl, and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more groups including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the terms "alkenyl" and "alkynyl" refer to straight and branched carbon chains having from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetylenyl, propynyl, -1-butynyl, -2-butynyl, -1-pentynyl, -2-pentynyl, and -3-methyl-1 butynyl.

Alkenyl and alkynyl groups, whether alone or as part of another group, can be optionally substituted with one or more groups, preferably 1 to 3 groups (and any additional substituents selected from halogen), including but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkyenl, —$C_2$-$C_8$ alkynyl, or -aryl and wherein said —O—($C_1$-$C_8$ alkyl), —O—($C_2$-$C_8$ alkenyl), —O—(C$_2$-C$_8$ alkynyl), -aryl, —C$_1$-C$_8$ alkyl, —C$_2$-C$_8$ alkenyl, and —C$_2$-C$_8$ alkynyl groups can be optionally further substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or -aryl.

Unless otherwise noted, the term "alkylene" refers to a saturated branched or straight chain hydrocarbon radical having from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohcxylcnc, and the like. Alkylene groups, whether alone or as part of another group, can be optionally substituted with one or more groups, preferably 1 to 3 groups (and any additional substituents selected from halogen), including, but not limited to, -halogen, —O—(C$_1$-C$_8$ alkyl), —O—(C$_2$-C$_8$ alkenyl), —O—C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', =O, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —O—(C$_1$-C$_8$ alkyl), —O—(C$_2$-C$_8$ alkenyl), —O—(C$_2$-C$_8$ alkynyl), -aryl, —C$_1$-C$_8$ alkyl, —C$_2$-C$_8$ alkenyl, and —C$_2$-C$_8$ alkynyl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or -aryl.

Unless otherwise noted, the term "alkenylene" refers to an optionally substituted alkylene group containing at least one carbon-carbon double bond. Exemplary alkenylene groups include, for example, ethenylene (—H=CH—) and propenylene (—CH=CH$_2$CH$_2$—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH$_2$C≡C—), and 4-pentynyl (—CH$_2$CH$_2$CH$_2$C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, -halogen, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —C$_1$-C$_8$ alkyl, —C$_2$-C$_8$ alkenyl, —C$_2$-C$_8$ alkynyl, O—(C$_1$-C$_8$ alkyl), —O—(C$_2$-C$_8$ alkenyl), —O—(C$_2$-C$_8$ alkynyl), and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or -aryl.

Unless otherwise noted, the term "arylenc" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group:

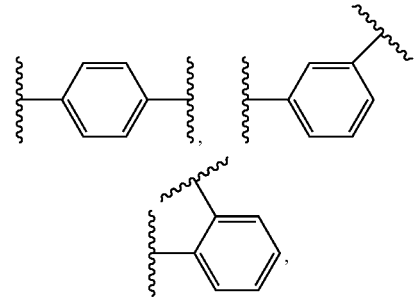

Typical "—(C$_1$-C$_8$ alkylene)aryl," "—(C$_2$-C$_8$ alkenylene)aryl", "and —(C$_2$-C$_8$ alkynylene)aryl" groups include, but are not limited to, benzyl, 2-phenylethan-1-yl, 2-phenylethen-1-yl, naphthylmethyl, 2-Naphthylethan-1-yl, 2-Naphthylethen-1-yl, naphthobenzyl, 2-Naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocylic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic.

Unless otherwise noted, the heterocycle is attached to its pendant group at any heteroatom or carbon atom that results in a stable structure.

Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 82:5566 (1960).

Unless otherwise noted, the term "heterocyclo" refers to an optionally substituted heterocycle group as defined above that is divalent (i.e., derived by the removal of two hydrogen atoms from the same or two different carbon atoms of a parent heterocyclic ring system).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

A heterocycle group, whether alone or as part of another group, can be optionally substituted with one or more groups, preferably 1 to 2 groups, including but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from —H, —$C_1$-$C_8$ alkyl, —$C_2$-$C_8$ alkenyl, alkynyl, or -aryl and wherein said —O—($C_1$-$C_8$ alkyl), —O—($C_2$-$C_8$ alkenyl), —O—($C_2$-$C_8$ alkynyl), —$C_1$-$C_8$ alkyl, —$C_2$-$C_8$ alkenyl, —$C_2$-$C_8$ alkynyl, and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or aryl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo [4,5], [5,5], [5,6] or [6,6] system, or 9 or 10 ring atoms arranged as a bicyclo [5,6] or [6,6] system. The term "carbocycle" includes, for example, a monocyclic carbocycle ring fused to an aryl ring (e.g., a monocyclic carbocycle ring fused to a benzene ring). Carbocyles preferably have 3 to 8 carbon ring atoms.

Carbocycle groups, whether alone or as part of another group, can be optionally substituted with, for example, one or more groups, preferably 1 or 2 groups (and any additional substituents selected from halogen), including, but not limited to, -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Examples of monocyclic carbocyclic substituents include -cyclopropyl, -cyclobutyl, -cyclopentyl, -1-cyclopent-1-enyl, -1-cyclopent-2-enyl, -1-cyclopent-3-enyl, cyclohexyl, -1-cyclohex-1-enyl, -1-cyclohex-2-enyl, -1-cyclohex-3-enyl, -cycloheptyl, -cyclooctyl, -1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

Unless otherwise indicated by context, a hyphen (-) designates the point of attachment to the pendant molecule. Accordingly, the term "($C_1$-$C_8$ alkylene)aryl" or "—$C_1$-$C_8$ alkylene(aryl)" refers to a $C_1$-$C_8$ alkylene radical as defined herein wherein the alkylene radical is attached to the pendant molecule at any of the carbon atoms of the alkylene radical and one of the hydrogen atoms bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. Groups that are substituted are so indicated.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

D. Dosing Regimen

The present invention provides, inter alia, a dosing regimen for the treatment of CD30-expressing hematologic cancers. The dosing regimen comprises a weekly dose of an antibody-drug conjugate as described herein of from about 0.8 mg/kg body weight to about 1.8 mg/kg body weight, 0.8 mg/kg body weight to about 1.6 mg/kg body weight, 0.8 mg/kg body weight to about 1.4 mg/kg body weight, 0.8 mg/kg body weight to about 1.2 mg/kg body weight, or more preferably from about 0.8 mg/kg body weight to about 1.0 mg/kg body weight for at least a three week period (e.g., 21 day period). The weekly dose can either be administered as a single weekly dose (once a week) or by split delivery (e.g., two or more times per week).

In some embodiments, the weekly dose of the antibody drug conjugate will be about 0.8 mg/kg body weight. In some embodiments, the weekly dose of the antibody drug conjugate will be about 0.9 mg/kg body weight. In some embodiments, the weekly dose of the antibody drug conjugate will be about 1.0 mg/kg body weight. In some embodiments, the weekly dose of the antibody drug conjugate will be about 1.1 mg/kg body weight. In some embodiments, the weekly dose of the antibody drug conjugate will be about 1.2 mg/kg body weight. In some embodiments, the weekly dose of the antibody drug conjugate will be about 1.3 mg/kg body weight. In some embodiments, the weekly dose of the antibody drug conjugate will be about 1.4 mg/kg body weight. In some embodiments, the weekly dose of the antibody drug conjugate will be about 1.5 mg/kg body weight. In some embodiments, the weekly dose of the antibody drug conjugate will be about 1.6 mg/kg body weight. In some embodiments, the weekly dose of the antibody drug conjugate will be about 1.7 mg/kg body weight. In some embodiments, the weekly dose of the antibody drug conjugate will be about 1.8 mg/kg body weight. In some embodiments, the weekly dose of the antibody drug conjugate will be 0.8, 0.9, 1, 1.1, 1.2, 1.3, 1.4, 1.5, 1.6, 1.7 or 1.8 mg/kg of the subject's body weight.

In some embodiments, the weekly dose is administered, as a split delivery or as a single weekly dose, for at least one three week (e.g., 21 day) treatment cycle. In some embodiments, the dose will be administered as a single weekly dose on days 1, 8, and 15 of a 21 day treatment cycle. Preferably, the weekly dose, as a split delivery or as a single weekly dose, is administered for two or more 21 day treatment cycles, even more preferably for three or more, four or more, five, or even six or more treatment cycles. In some embodiments, the weekly dose is administered for no more than 3, no more than 4, no more than 5, or no more than 6 treatment cycles. Preferably, there will a period of rest between treatment cycles. For example, in some preferred embodiments, the dosing regimen will be a total weekly dose of the antibody-drug conjugate of from about 0.8 mg/kg body weight to about 1.8 mg/kg body weight, 0.8 mg/kg body weight to about 1.6 mg/kg body weight, 0.8 mg/kg body weight to about 1.4 mg/kg body weight, 0.8 mg/kg body weight to about 1.2 mg/kg body weight or 0.8 mg/kg body weight to about 1.0 mg/kg body weight for at least two treatment cycles with a one week period of rest between each of the treatment cycles (e.g., six single weekly doses during an eight week time period). In some embodiments, the treatment cycle will be greater than 21 days. The weekly dose can be administered as a single weekly dose (once a week) or by split delivery (e.g., two or more times per week).

Instead of referring to the treatment cycle as a three week treatment cycle with a one week period of rest between treatment cycles, the treatment cycle can be referred to as a 4 week (28 day) treatment cycle where the antibody-drug conjugate is delivered 3 out of 4 weeks in the 4 week treatment cycle. Accordingly, in some embodiments, the dose is administered weekly, as a split delivery or as a single weekly dose, 3 out of 4 weeks in a 4 week treatment cycle. In some embodiments, the dose will be administered as a single weekly dose on days 1, 8, and 15 of a 28 day treatment cycle. Preferably, the weekly dose, as a split delivery or as a single weekly dose, is administered for two or more four week treatment cycles, even more preferably for three or more, four or more, five or more, or even six or more four week treatment cycles (e.g., 2, 3, 4, 5, or 6 consecutive treatment cycles). In some embodiments, the weekly dose is administered for no more than 3, no more than 4, no more than 5, or no more than 6 treatment cycles. For example, in some preferred embodiments, the dosing regimen will be a weekly dose, as a split delivery or as a single weekly dose, for a total weekly dose of from about 0.8 mg/kg body weight to about 1.8 mg/kg body weight, 0.8 mg/kg body weight to about 1.6 mg/kg body weight, 0.8 mg/kg body weight to about 1.4 mg/kg body weight, 0.8 mg/kg body weight to about 1.2 mg/kg body weight or 0.8 mg/kg body weight to about 1.0 mg/kg body weight of the antibody-drug conjugate, 3 out of 4 weeks, for at least two four week treatment cycles (e.g., six single weekly doses an eight week time period). In some preferred embodiments, the dosing regimen will be a weekly dose, as a split delivery or as a single weekly dose, for a total weekly dose of from about 0.8 mg/kg body weight to about 1.8 mg/kg body weight, 0.8 mg/kg body weight to about 1.6 mg/kg body weight, 0.8 mg/kg body weight to about 1.4 mg/kg body weight, 0.8 mg/kg body weight to about 1.2 mg/kg body weight or 0.8 mg/kg body weight to about 1.0 mg/kg body weight of the antibody-drug conjugate, 3 out of 4 weeks, for one, two, three, four, or five four week treatment cycles (e.g., six single weekly doses in an eight week time period, nine single weekly doses in a twelve week time period, twelve single weekly doses in a sixteen week time period).

Following or during one or more treatment cycles (e.g., during days 21-28 of the second treatment cycle), the subject can be evaluated (e.g., through clinical or diagnostic testing) to determine whether the subject should remain on the treatment schedule. For example, following or during one or more 28 day treatment cycles (e.g., 1, 2, 3, 4, 5, or 6 28 day treatment cycles), the subject can be evaluated (e.g., a clinical and/or diagnostic evaluation). Depending on the evaluation, the subject will discontinue treatment, continue on treatment with additional treatment cycles, or commence maintenance therapy. If the subject continues treatment, the subject can be further evaluated following one or more additional treatment cycles. Depending on each successive evaluation, the subject will discontinue treatment, continue on treatment with additional treatment cycles, or commence maintenance therapy.

The present invention encompasses embodiments wherein the subject remains on the weekly treatment cycle (e.g., the four week treatment cycle) following an evaluation indicating that the subject has no detectable cancer, for example, following a diagnostic test that is negative for the CD30 expressing cancer (i.e., the diagnostic test is unable to detect any cancer in the subject). For example, in some embodiments, the subject will remain on the weekly treatment cycle for at least 2, 3, 4, 5, 6, 7, 8, 9, 10, 11, 12 or more treatment cycles following such an evaluation. In some embodiments, the subject will remain on the weekly treatment cycle for at least two but no more than 3, no more than 4, no more than 5, or no more than 6 treatment cycles. One example of a diagnostic test used for determining the presence and severity of cancers is positron emission tomography (PET).

In some embodiments, the subject will commence maintenance therapy following one or more, preferably two or more, (e.g, following 1, 2, 3, 4, 5, or 6) treatment cycles (e.g., the four week treatment cycle). In some embodiments, the subject will commence maintenance therapy following an evaluation indicating that the subject has little or no detectable cancer, e.g., following an evaluation indicating that the subject has had a complete response. As used herein, maintenance therapy refers to therapy with the antibody-drug conjugate but at a reduced administration schedule at either the same or different dosages. During maintenance therapy, the antibody-drug conjugate is preferably administered once every two weeks, once every three weeks, once every four weeks, once every five weeks, once every 6 weeks, once every 7 weeks, or once every 8 weeks. Following these maintenance therapy cycles, the subject can be further evaluated (e.g., through clinical or diagnostic testing) to determine whether the subject should remain on the maintenance therapy, continue with regular treatment or discontinue treatment. In some embodiments, maintenance therapy will be once every three weeks to six weeks. The dosage of the antibody drug conjugate administered during maintenance therapy can range, for example, from about 0.3 mg/kg body weight to about 2.0 mg/kg body weight, preferably from about 0.6 mg/kg body weight to about 1.8 mg/kg body weight, preferably from about 1.2 mg/kg body weight to about 2.0 mg/kg body weight, more preferably from about 1 mg/kg body weight to about 1.8 mg/kg body weight per dose, with 1.8 mg/kg being an exemplary dose.

In some embodiments, following conclusion of the weekly treatment at a dosage of the antibody drug conjugate of from about 0.8 mg/kg body weight to about 1.8 mg/kg body weight, more preferably a dosage of from about 0.8 mg/kg body weight to about 1.2 mg/kg body weight and evaluation, the subject will begin a maintenance therapy which comprises administration of the antibody-drug conjugate once every three to six weeks at a dosage of from about 0.3 mg/kg body weight to about 2 mg/kg body weight, preferably from about 0.6 mg/kg body weight to about 1.8 mg/kg body weight, preferably from about 1.2 mg/kg body weight to about 2.0 mg/kg body weight, more preferably from about 1 mg/kg body weight to about 1.8 mg/kg body weight with about 1.8 mg/kg being preferred. In some embodiments, following conclusion of the weekly treatment (e.g., for one, two, three, four or five treatment cycles), the subject will begin a once every three week administration schedule (e.g., treatment on day 1 of a three week maintenance therapy cycle) of the antibody drug conjugate at a dosage of from about 0.4 mg/kg body weight to about 2 mg/kg body weight, from about 1.2 mg/kg body weight to about 2.0 mg/kg body weight, or from about 1 mg/kg body weight to about 1.8 mg/kg body weight with about 1.8 mg/kg being preferred.

Accordingly, the present invention encompasses embodiments wherein a subject will be administered a weekly dose, as a split delivery or as a single weekly dose, of the antibody drug conjugate for a total weekly dose of from about 0.8 mg/kg of the subject's body weight to about 1.8 mg/kg of the subject's body weight, about 0.8 mg/kg body weight to about 1.6 mg/kg body weight, about 0.8 mg/kg body weight to about 1.4 mg/kg body weight, about 0.8 mg/kg body weight to about 1.2 mg/kg body weight or about 0.8 mg/kg body weight to about 1.0 mg/kg body weight, 3 out of 4 weeks, for one, two, three, four, five, or six 28 day treatment cycles followed by administration of an every three to six week dose, preferably every three week dose, of antibody drug conjugate at a dose of from about 0.4 mg/kg body weight to about 2 mg/kg body weight, from about 1.2 mg/kg body weight to about 2.0 mg/kg body weight, or from about 1.0 mg/kg body weight to about 1.8 mg/kg body weight per dose for 2 or more maintenance therapy cycles. In some embodiments, the weekly administration cycle will be for 2, 3, 4, 5, 6, 7, 8, 9 or 10 or more treatment cycles and the every three week administration schedule will be for 2, 3, 4, 5, 6, 7, 8, 9 or 10 or more maintenance therapy cycles. In some embodiments, the weekly administration cycle will be for no more than 2, 3, 4, 5, or 6 treatment cycles.

The present invention encompasses embodiments wherein a subject will be administered a weekly dose, as a split delivery or as a single weekly dose, of the antibody drug conjugate at a total weekly dose of dose of from about 0.8 mg/kg of the subject's body weight to about 1.2 mg/kg 3 out of 4 weeks (e.g., on days 1, 8, and 15 of a 28 day treatment cycle) for one, two, three, four, five, or six 28 day treatment cycles followed by administration of an every three to six week dose, preferably every three week dose, of antibody drug conjugate at a dose of about 1.8 mg/kg per body weight for 2 or more maintenance therapy cycles (e.g., a dose of about 1.8 mg/kg per body weight every three weeks for two or more three week maintenance therapy cycles).

The present invention encompasses embodiments wherein the subject to be treated by the present methods is being treated with a anti-CD30 vc-PAB MMAE antibody-drug conjugate of the present invention but at a schedule other than the weekly dosing regimen (e.g., administration of the antibody drug conjugate at a dose of about 1.8 mg/kg body weight every three weeks for one or more three week therapy cycles) and is switched to a weekly dosing regimen as described herein for no more than 1, 2, 3, 4, 5, or 6 treatment cycles. Following the weekly dosing regimen, the patient can optionally commence maintenance therapy as described herein.

The present invention also encompasses embodiments wherein following treatment with the antibody-drug conjugate and prior to commencement of maintenance therapy, the subject will undergo a stem cell transplant. Accordingly, in some embodiments, following two or more treatment cycles (e.g., following 1, 2, 3, 4, 5 or 6 treatment cycles) and following an evaluation indicating that the subject is eligible for a stem cell transplant, the subject will undergo a stem cell transplant. Following the transplant, the subject can commence maintenance therapy. Maintenance therapy will commence post transplant and prior to any detectable relapse of the cancer.

The antibody-drug conjugate is preferably administered as a monotherapy. By the term "monotherapy" it is meant that the antibody drug conjugate is the only anti-cancer agent administered to the subject during the treatment cycle. Other therapeutic agents, however, can be administered to the subject. For example, anti-inflammatory agents or other agents administered to a subject with cancer to treat symptoms associated with cancer, but not the underlying cancer itself, including, for example inflammation, pain, weight loss, and general malaise can be administered during the period of monotherapy. A subject being treated by the present methods will preferably have completed any prior treatment with anti-cancer agents before administration of the antibody drug conjugate. In some embodiments, the subject will have completed any prior treatment with anti-cancer agents at least 1 week (preferably 2, 3, 4, 5, 6, 7, or 8 weeks) prior to treatment with the antibody drug conjugate. The subject will also, preferably, not be treated with any additional anti-cancer agents for at least 2 weeks (preferably at least 3, 4, 5, 6, 7, or 8 weeks) following completion of the first treatment cycle with the antibody drug conjugate and preferably for at least 2 weeks (preferably at least 3, 4, 5, 6, 7, or 8 weeks) following completion of the last dose of the antibody drug conjugate.

E. Subjects

The methods of the present invention encompass administering an anti-CD30 vc-PAB-MMAE antibody-drug conjugate to a subject for the treatment of a CD30-expressing hematologic cancer. After administration of the antibody-drug conjugate to a subject and binding of the anti-CD30 antibody to a CD30 expressing cancer cell, the antibody drug conjugate internalizes into the cell, and the drug is released.

A CD30-expressing hematologic cancer refers to a hematologic cancer that expresses the CD30 antigen. The CD30 antigen is expressed in large numbers on tumor cells of select lymphomas and leukemias. Hodgkin lymphoma, anaplastic large-cell lymphoma, and/or acute or lymphomatous forms of adult T-cell leukemia are examples of CD30-expressing hematologic cancers that can be treated by the present methods.

The subjects to be treated with the methods of the present invention are those that have been diagnosed with a CD30 expressing hematologic cancer or are suspected of having a CD30-expressing hematologic cancer. Diagnosis can be by methods known in the art, including, for example, lymph node biopsy. After Hodgkin lymphoma is diagnosed, for example, a subject can be classified according to stage of disease using one of the known classification schemes. The Cotswolds staging classification scheme is one such classification scheme. The methods of the present invention can be used to treat a subject classified in any stage of disease, including a subject with advanced stage disease.

The methods of the present invention encompass treating a subject who is newly diagnosed and has not previously been treated for a CD30-expressing hematologic cancer.

The methods of the present invention can be used to treat subjects with a refractory and/or relapsed CD30-expressing hematologic cancer.

A subject with a refractory CD30-expressing hematologic cancer is a subject who has not responded to a previous anti-cancer therapy, i.e., the subject continues to experience disease progression despite therapy.

A subject with a relapsed CD30-expressing hematologic cancer is a subject who has responded to a prior anti-cancer therapy for the disease at one point, but has had a reoccurence or further progression of disease following the response.

The methods of the present invention encompass, for example, treating a subject who has previously been treated with a first-line chemotherapy regimen and/or a salvage regimen and/or experimental treatment for the CD30-expressing hematologic cancer. First line chemotherapeutic regimens for Hodgkin lymphoma include, for example, the ABVD regimen (Bonadonna and Santoro, Cancer Treat Rev 1982; 9:21-35), the BEACOPP regimen (Diehl et al., N Engl J Med 2003; 348:2386-2395), the escalated BEACOPP regimen (Diehl et al., N Engl J Med 2003; 348:2386-2395), the MOPP regimen (Devita et al., Ann Inter Med 1970: 73:881-895), and the Stanford V regimen (Horning et al., J Clin Oncol 2000; 18:972-980). Salvage chemotherapy regimens and experimental regimens include, for example, the ESHAP regimen (Aparicio et al., Ann Ocol 1999; 10:593-595), the modified Stanford V regimen (Aviles et al., Med Oncol 2001; 18:261-267), the GDP regimen (Baetz et al., Ann Oncol 2003; 14:1762-1767), the Mini-Beam regimen (Colwill et al., J Clin Oncol 1995; 13:396-402, Fernandez-Jimenez et al., Haematologica 1999; 84:1007-1011), the MIME regimen (Enblad et al., Eur J Haematol 1998; 60:166-171), the MINE regimen (Ferme et al., Ann Oncol 1995; 6:543-549), the IEE regimen (Jackson et al., Leuk Lymphoma 2000; 37:561-570), the DHAP regimen (Josting et al., Ann Oncol 2002; 13:1628-1635), the ICE regimen (Moskowitz et al., Semin Oncol 2004; 31(suppl):54-59), the HVP regimen (Oyan et al., Biol Blood Marrow Transplant 2005; 11:688-697), the IVE regimen (Proctor et al., Eur J Haematol 2001; 64(suppl):28-32), the VIP regimen (Ribrag et al., Bome Marrow Transplant 1998; 21:969-974), the ASHAP regimen (Rodriguez et al., Blood 1999; 93:3632-3636), the Dexa-BEAM regimen (Schmitz et al., Lancet 2002; 359:2065-2071), the CEP regimen (Szanto et al., Oncology 1991; 48:456-458), the CN30P regimen (Walewski et al., Med Oncol. 2000; 17:195-202), the MVC regimen (Wiernik et al., Cancer J Sci Am 1998; 4:254-260) and gemcitabine (Savage et al., Annals of Oncology 2000; 11:595-597).

The methods of the present invention also encompass treating a subject who has previously undergone a stem cell transplant. In some embodiments, the methods encompass treating a subject who has undergone a stem cell transplant for treatment of a CD30-expressing hematologic cancer and who, at the time, of treatment has no detectable signs of cancer. The methods also encompass treating a subject who has previously undergone a stem cell transplant but has relapsed.

F. Anti-CD30 Antibodies

Anti-CD30 antibodies suitable for use in accordance with the present compositions and methods include any antibody that specifically binds to the CD30 antigen.

In some embodiments, anti-CD30 antibodies of the present invention not only immunospecifically bind CD30 but also can exert cytostatic and/or cytotoxic effect on cancerous cells, for example, malignant cells in HL. In some such embodiments, the cytostatic or cytotoxic effect is complement-independent and can be achieved in the absence of (i) conjugation to a cytostatic or cytotoxic agent and (ii) effector cells. For example, in some such embodiments, the cytostatic or cytotoxic effect is not a result of antibody effector function but, for example, a result of signaling activity.

Anti-CD30 antibodies of the present invention are preferably monoclonal and can include, for example, chimeric (e.g., having a human constant region and mouse variable region), humanized, or human antibodies. The immunoglobulin molecule is of the IgG type and can be any subclass (e.g., IgG1, IgG2, IgG3, IgG4) of immunoglobulin molecule and variants thereof. The immunoglobulin molecule is preferably an IgG1.

The antibodies of the present invention can be generated by any suitable method known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammerling, et al., in: Monoclonal Antibodies and T-Cell Hybridomas 563-681 (Elsevier, N.Y., 1981) (said references incorporated by reference in their entireties).

Any method known in the art for the synthesis of proteins, e.g., recombinant expression techniques, can be used to generate the anti-CD30 antibodies of the present invention.

Once a CD30-binding protein is identified, if desired, its ability (alone or when multimerized or fused to a dimerization or multimerization domain) to elicit a cytostatic or cytotoxic effect on CD30-expressing cancerous cells can be determined by contacting a culture of an CD30-expressing cancer cell line, such as L428, L450, HLLM2 or KM-H2, with the protein. Culture conditions are most preferably about 5,000 cells in a culture area of about 0.33 cm$^2$, and the contacting period being approximately 72 hours. The culture is then exposed to 0.5 μCi of $^3$H-thymidine during the final 8 hours of the 72-hour period and the incorporation of $^3$H-thymidine into cells of the culture is measured. The protein has a cytostatic or cytotoxic effect on the cell line if the cells of the culture have reduced $^3$H-thymidine incorporation compared to cells of the same cell line cultured under the same conditions but not contacted with the protein. There are many other cytotoxicity assays known to those of skill in the art. Any one of them can be used in the present methods.

Exemplary anti-CD30 antibodies include, but are not limited to, humanized or chimeric AC10 or HeFi-1 antibodies. Murine AC10 has been deposited under ATCC Accession Number PTA-6679.

An exemplary anti-CD30 antibody comprises one or more (1, 2, 3, 4, 5, or 6) CDRs of murine HeFi-1 (SEQ ID NO:20, SEQ ID NO:22; SEQ ID NO:24; SEQ ID NO:28, SEQ ID NO:30 or SEQ ID NO:32) or murine AC10 (SEQ ID NO:4; SEQ ID NO:6; SEQ ID NO:8; SEQ ID NO:12; SEQ ID NO:14; or SEQ ID NO:16). In some embodiments, the anti-CD30 antibody comprises the heavy and/or light chain variable regions of murine HeFi-1 (SEQ ID NO:18 or SEQ ID NO:26) or murine AC10 (SEQ ID NO:2 or SEQ ID NO:10). A table indicating the region of AC10 or HeFi-1 to which each SEQ ID NO corresponds to is provided below.

TABLE 1

| MOLECULE | NUCLEOTIDE OR AMINO ACID | SEQ ID NO |
|---|---|---|
| AC10 Heavy Chain Variable Region | Nucleotide | 1 |
| AC10 Heavy Chain Variable Region | Amino Acid | 2 |
| AC10 Heavy Chain-CDR1(H1) | Nucleotide | 3 |
| AC 10 Heavy Chain-CDR1(H1) | Amino Acid | 4 |
| AC 10 Heavy Chain-CDR2(H2) | Nucleotide | 5 |
| AC 10 Heavy Chain-CDR2(H2) | Amino Acid | 6 |
| AC 10 Heavy Chain-CDR3(H3) | Nucleotide | 7 |
| AC 10 Heavy Chain-CDR3(H3) | Amino Acid | 8 |
| AC 10 Light Chain Variable Region | Nucleotide | 9 |
| AC 10 Light Chain Variable Region | Amino Acid | 10 |
| AC 10 Light Chain-CDR1(L1) | Nucleotide | 11 |
| AC 10 Light Chain-CDR1(L1) | Amino Acid | 12 |
| AC 10 Light Chain-CDR2(L2) | Nucleotide | 13 |
| AC 10 Light Chain-CDR2(L2) | Amino Acid | 14 |
| AC 10 Light Chain-CDR3(L3) | Nucleotide | 15 |
| AC 10 Light Chain-CDR3(L3) | Amino Acid | 16 |
| HeFi-1 Heavy Chain Variable Region | Nucleotide | 17 |
| HeFi-1 Heavy Chain Variable Region | Amino Acid | 18 |
| HeFi-1 Heavy Chain-CDR1(H1) | Nucleotide | 19 |
| HeFi-1 Heavy Chain-CDR1(H1) | Amino Acid | 20 |
| HeFi-1 Heavy Chain-CDR2(H2) | Nucleotide | 21 |
| HeFi-1 Heavy Chain-CDR2(H2) | Amino Acid | 22 |
| HeFi-1 Heavy Chain-CDR3(H3) | Nucleotide | 23 |
| HeH-1 Heavy Chain-CDR3(H3) | Amino Acid | 24 |
| HeFi-1 Light Chain Variable Region | Nucleotide | 25 |
| HeFi-1 Light Chain Variable Region | Amino Acid | 26 |
| HeFi-1 Light Chain-CDR1(L1) | Nucleotide | 27 |
| HeFi-1 Light Chain-CDR1(L1) | Amino Acid | 28 |
| HeFi-1 Light Chain-CDR2(L2) | Nucleotide | 29 |
| HeFi-1 Light Chain-CDR2(L2) | Amino Acid | 30 |
| HeFi-1 Light Chain-CDR3(L3) | Nucleotide | 31 |
| HeFi-1 Light Chain-CDR3(L3) | Amino Acid | 32 |
| Human gamma I constant region | Amino Acid | 33 |
| Human kappa constant region | Amino Acid | 34 |

In a specific embodiment, the invention encompasses an antibody comprising a heavy chain variable domain, said variable domain comprising (a) a set of three CDRs, in which said set of CDRs comprises SEQ ID NO:4, 6, or 8 or comprises amino acid sequences that are substantially identical to the amino acid sequences set forth in SEQ ID NO:4, 6, or 8 and (b) a set of four framework regions, in which said set of framework regions differs from the set of framework regions in murine monoclonal antibody AC10, and in which said antibody immunospecifically binds CD30.

In a specific embodiment, the invention encompasses an antibody comprising a heavy chain variable domain, said variable domain comprising (a) a set of three CDRs, in which said set of CDRs comprises SEQ ID NO:20, 22 or 24 or comprises amino acid sequences that are substantially identical to the amino acid sequences set forth in SEQ ID NO:20, 22, or 24 and (b) a set of four framework regions, in which said set of framework regions differs from the set of framework regions in murine monoclonal antibody HeFi-1, and in which said antibody immunospecifically binds CD30.

In a specific embodiment, the invention encompasses an antibody comprising a light chain variable domain, said variable domain comprising (a) a set of three CDRs, in which said set of CDRs comprises SEQ ID NO:12, 14 or 16 or comprises amino acid sequences that are substantially identical to the amino acid sequences set forth in SEQ ID NO:12, 14, or 16, and (b) a set of four framework regions, in which said set of framework regions differs from the set of framework regions in murine monoclonal antibody AC10, and in which said antibody immunospecifically binds CD30.

In a specific embodiment, the invention encompasses an antibody comprising a light chain variable domain, said variable domain comprising (a) a set of three CDRs, in which said set of CDRs comprises SEQ ID NO:28, 30, or 32 or comprises amino acid sequences that are substantially identical to the amino acid sequences set forth in SEQ ID NO:28, 30, or 32, and (b) a set of four framework regions, in which said set of framework regions differs from the set of framework regions in murine monoclonal antibody HeFi-1, and in which said antibody immunospccifically binds CD30.

In certain embodiments, the anti-CD30 antibody comprises a gamma I constant region, (e.g., huCγ1, SwissProt accession number P01857, incorporated herein by reference in its entirety) and a human kappa constant region (e.g., huCκ, PID G185945, incorporated herein by reference in its entirety).

The present invention encompasses embodiments wherein a chimeric AC10 antibody comprises the heavy chain variable region set forth in SEQ ID NO:2, the light chain variable region set forth in SEQ ID NO:10, the human gamma I constant region set forth in SEQ ID NO:33 (or amino acids 1 to 329 of SEQ ID NO:33) and the human kappa constant region set forth in SEQ ID NO:34.

Additionally, the antibodies can also be described or specified in terms of their primary structures. In some embodiments, the variable regions of the anti-CD30 antibodies will have at least 80%, at least 85%, at least 90%, at least 95% and most preferably at least 98% identity (as calculated using methods known in the art and described herein) to the variable regions of murine AC10 or HeFi-1.

Exemplary anti-CD30 antibodies include functional derivatives or analogs of AC10 and HeFi-1. As used herein, the term "functional" in this context indicates that the functional derivate or analog of AC10 and HeFi-1 is capable of specific binding to CD30.

Antibodies for use in the present invention include those that competitively inhibit binding of murine AC10 or HeFi-1 to CD30 as determined by any method known in the art for determining competitive binding. For example, the antibody can inhibit binding of AC10 or HcFi-1 to CD30 by at least 50%, at least 60%, at least 70%, at least 80%, at least 85%, at least 90%, or even at least 95%.

G. Antibody-Drug Conjugates

The methods described herein encompass the use of antibody drug conjugates comprising an anti-CD30 antibody, covalently linked to MMAE through a vc-PAB linker. The antibody drug conjugates are delivered to the subject as a pharmaceutical composition.

The antibody-drug conjugates of the present invention have the following formula:

loading taking into account all of the antibody present in the pharmaceutical composition is about 4. P ranges from about 3 to about 5, more preferably from about 3.6 to about 4.4, even more preferably from about 3.8 to about 4.2. P can be about 3, about 4, or about 5. The average number of drugs per antibody in preparation of conjugation reactions may be characterized by conventional means such as mass spectroscopy, ELISA assay, and HPLC. The quantitative distribution of antibody-drug conjugates in terms of p may also be determined. In some instances, separation, purification, and characterization of homogeneous antibody-drug-conjugates where p is a certain value from antibody-drug-conjugates with other drug loadings may be achieved by means such as reverse phase HPLC or electrophoresis.

The Stretcher unit (A), is capable of linking an antibody unit to the valine-citrulline amino acid unit via a sulfhydryl group of the antibody. Sulfhydryl groups can be generated, for example, by reduction of the interchain disulfide bonds of an anti-CD30 antibody. For example, the Stretcher unit can be linked to the antibody via the sulfur atoms generated from reduction of the interchain disulfide bonds of the antibody. In some embodiments, the Stretcher units are linked to the antibody solely via the sulfur atoms generated from reduction of the interchain disulfide bonds of the antibody. In some embodiments, sulfhydryl groups can be generated by reaction of an amino group of a lysine moiety of an anti-CD30 antibody with 2-iminothiolane (Traut's reagent) or other sulfhydryl generating reagents. In certain embodiments, the anti-CD30 antibody is a recombinant antibody and is engineered to carry one or more lysines. In certain other embodiments, the recombinant anti-CD30 antibody is engineered to carry additional sulfhydryl groups, e.g., additional cysteines.

The synthesis and structure of MMAE is described in U.S. Pat. No. 6,884,869 incorporated by reference herein in its entirety and for all purposes. The synthesis and structure of exemplary Stretcher units and methods for making antibody drug conjugates are described in, for example, U.S. Publi-

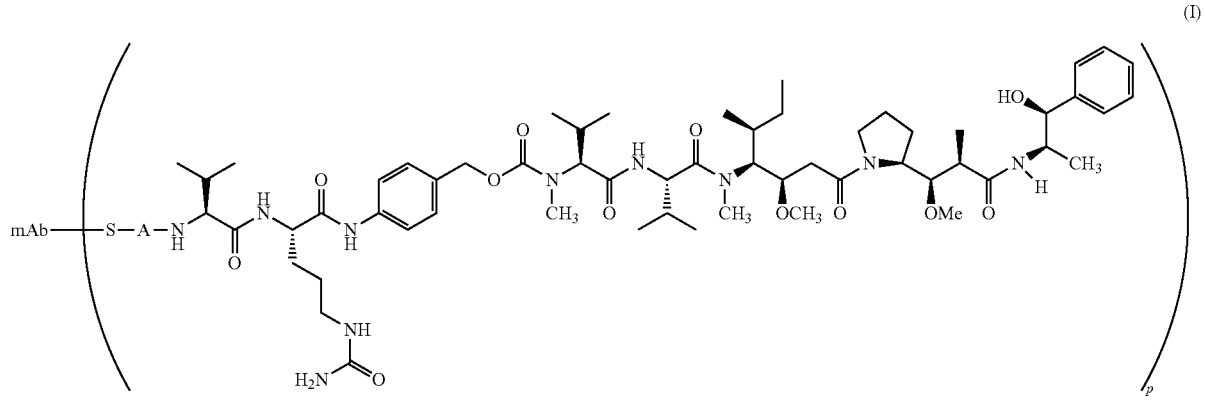

(I)

or a pharmaceutically acceptable salt thereof;
wherein:
mAb is an anti-CD30 antibody,
S is a sulfur atom of the antibody
A- is a Stretcher unit,
p is from about 3 to about 5.

The drug loading is represented by p, the average number of drug molecules per antibody in a pharmaceutical composition. For example, if p is about 4, the average drug cation Nos. 2006/0074008 and 2009/0010945 each of which is incorporated herein by reference in its entirety.

Representative Stretcher units are depicted within the square brackets of Formulas IIIa and IIIb, wherein L-, —W—, —Y—, -D, w and y are as defined above, and $R_{17}$ is selected from —$C_1$-$C_{10}$ alkylene-, —$C_1$-$C_{10}$ alkenylene-, —$C_1$-$C_{10}$ alkynylene-, -carbocyclo-, —O—($C_1$-$C_8$ alkylene)-, O—($C_1$-$C_8$ alkenylene)-, —O—($C_1$-$C_8$ alkynylene)-, -arylene-, —$C_1$-$C_{10}$ alkylene-arylene-, —$C_2$-$C_{10}$ alkenylene-arylene, —$C_2$-$C_{10}$ alkynylene-arylene, -arylene, —$C_1$-$C_{10}$ alkylene-, -arylene-$C_2$-$C_{10}$ alkenylene-, -arylene-$C_2$-$C_{10}$ alkynylene-, —$C_1$-$C_{10}$ alkylene-(carbocyclo)-, —$C_2$-$C_{10}$ alkenylene-(carbocyclo)-, —$C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, -heterocyclo-, —$C_1$-$C_{10}$ alkylene-(heterocyclo)-, —$C_2$-$C_{10}$ alkenylene-(heterocyclo)-, —$C_2$-$C_{10}$ alkynylene-(heterocyclo)-, -(heterocyclo)-$C_1$-$C_{10}$ alkylene-, -(heterocyclo)-$C_1$-$C_{10}$ alkenylene-, -(heterocyclo)-$C_1$-$C_{10}$ alkynylene-, or —($CH_2CH_2O$)$_r$—, —($CH_2CH_2O$)$_r$—$CH_2$—, and r is an integer ranging from 1-10, wherein said alkyl, alkenyl, alkynyl, alkylene, alkenylene, alkynyklene, aryl, carbocyle, carbocyclo, heterocyclo, and arylene radicals, whether alone or as part of another group, are optionally substituted.

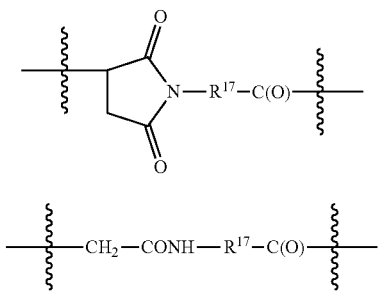

IIIa

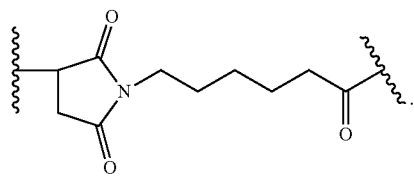 [SMILES: *C(=O)CCCCCN1C(=O)CC(*)C1=O]

IIIb

An illustrative Stretcher unit is that of Formula IIIa wherein $R^{17}$ is —($CH_2$)$_5$—:

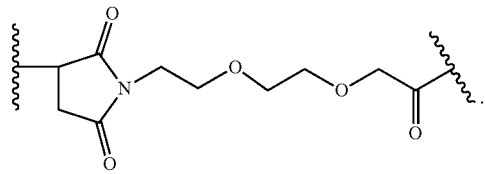 [SMILES: *C(=O)COCCOCCN1C(=O)CC(*)C1=O]

Another illustrative Stretcher unit is that of Formula IIIa wherein $R^{17}$ is —($CH_2CH_2O$)$_r$—$CH_2$—; and r is 2:

An illustrative Stretcher unit is that of Formula IIIa wherein $R^{17}$ is -arylene- or arylene-$C_1$-$C_{10}$ alkylene-. In some embodiments, the aryl group is a phenyl group.

Still another illustrative Stretcher unit is that of Formula IIIb wherein $R^{17}$ is —($CH_2$)$_5$—:

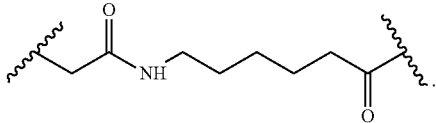 [SMILES: *CC(=O)NCCCCCC(*)=O]

One way that the Stretcher unit can be linked to the antibody unit is via a disulfide bond between a sulfur atom of the antibody unit and a sulfur atom of the Stretcher unit. In some embodiments, the sulfur atom is from an internal cysteine residue of the antibody. In some other embodiments, the sulfur atom is from a cysteine residue that has been engineered into the antibody.

A representative Stretcher unit is depicted within the square brackets of Formula IV, wherein $R^{17}$ is as defined above.

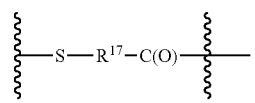

IV

It should be noted that throughout this application, the S moiety in the formula below refers to a sulfur atom of the antibody, unless otherwise indicated by context.

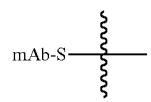

In a particularly preferred embodiment, of the present invention, the strectcher is of Formula IIIa and the antibody drug conjugate is a MC-vc-PAB-MMAE antibody drug conjugate as follows wherein p is from about 3 to about 5, preferably from 3.8 to 4.2. The S moiety refers to a sulfur atom of the antibody.

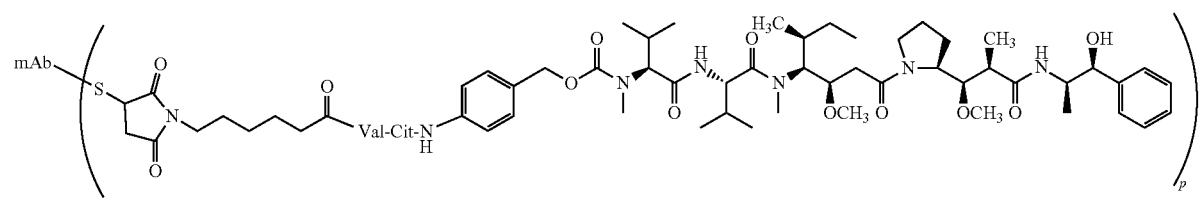

In a particularly preferred embodiment, the antibody is a chimeric or humanized AC10 antibody. In a particularly preferred embodiment, the S moiety is generated by reduction of the interchain disulfide bonds of the antibody.

H. Pharmaceutical Compositions and Formulations

Various delivery systems can be used to administer antibody-drug conjugates. In certain preferred embodiments of the present invention, administration of the antibody-drug conjugate compound is by intravenous infusion. In some embodiments, administration is by a two hour intravenous infusion.

The antibody-drug conjugate compound can be administered as a pharmaceutical composition comprising one or more pharmaceutically compatible ingredients. For example, the pharmaceutical composition typically includes one or more pharmaceutically acceptable carriers, for example, water-based carriers (e.g., sterile liquids). Water is a more typical carrier when the pharmaceutical composition is administered intravenously.

The composition, if desired, can also contain, for example, saline salts, buffers, salts, nonionic detergents, and/or sugars. Examples of suitable pharmaceutical carriers are described in "Remington's Pharmaceutical Sciences" by E. W. Martin. The formulations correspond to the mode of administration.

The present invention provides, for example, pharmaceutical compositions comprising a therapeutically effective amount of the antibody-drug conjugate, a buffering agent, optionally a cryoprotectant, optionally a bulking agent, optionally a salt, and optionally a surfactant. Additional agents can be added to the composition. A single agent can serve multiple functions. For example, a sugar, such as trehalose, can act as both a cryoprotectant and a bulking agent. Any suitable pharmaceutically acceptable buffering agents, surfactants, cyroprotectants and bulking agents can be used in accordance with the present invention.

In addition to providing methods for treating a CD30-expressing cancer, the present invention provides antibody drug conjugate formulations including drug conjugate formulations that have undergone lyophilization, or other methods of protein preservation, as well as antibody drug formulations that have not undergone lyophilization.

In some embodiments, the antibody drug conjugate formulation comprises (i) about 1-25 mg/ml, preferably about 3 to about 10 mg/ml of an antibody-drug conjugate (e.g., an antibody-drug conjugate of formula I or a pharmaceutically acceptable salt thereof), (ii) about 5-50 mM, preferably about 10 mM to about 25 mM of a buffer selected from a citrate, phosphate, or histidine buffer or combinations thereof, preferably sodium citrate, potassium phosphate, histidine, histidine hydrochloride, or combinations thereof, (iii) about 3% to about 10% sucrose or trehalose or combinations thereof, (iv) optionally about 0.05 to 2 mg/ml of a surfactant selected from polysorbate 20 or polysorbate 80 or combinations thereof; and (v) water, wherein the pH of the composition is from about 5.3 to about 7, preferably about 6.6.

In some embodiments, an antibody drug conjugate formulation will comprise about 1-25 mg/ml, preferably about 3 to about 10 mg/ml, even more preferably about 5 mg/ml of an antibody-drug conjugate, (ii) about 10 mM to about 25 mM of a buffer selected from sodium citrate, potassium phosphate, histidine, histidine hydrochloride or combinations thereof, (iii) about 3% to about 7% trehalose or sucrose or combinations thereof, optionally (iv) about 0.05 to about 1 mg/ml of a surfactant selected from polysorbate 20 or polysorbate 80, and (v) water, wherein the pH of the composition is from about 5.3 to about 7, preferably about 6.6.

In some embodiments, an antibody drug conjugate formulation will comprise about 5 mg/ml of an antibody-drug conjugate, (ii) about 10 mM to about 25 mM of a buffer selected from sodium citrate, potassium phosphate, histidine, histidine hydrochloride or combinations thereof, (iii) about 3% to about 7% trehalose, optionally (iv) about 0.05 to about 1 mg/ml of a surfactant selected from polysorbate 20 or polysorbate 80, and (v) water, wherein the pH of the composition is from about 5.3 to about 7, preferably about 6.6.

The antibody drug conjugate formulation can, for example, comprise (or consist essentially of) about 5 mg/ml of an antibody-drug conjugate, (ii) about 20 mM sodium citrate (iii) about 6% to about 7% trehalose (about 70 mg/ml), (iv) about 0.1 to 0.3 mg/ml of a surfactant selected from polysorbate 20 or polysorbate 80 (preferably polysorbate 80), and (v) water, wherein the pH of the composition is from about 5.3 to about 7, preferably about 6.6.

Any of the formulations described above can be stored in a liquid or frozen form and can be optionally subjected to a preservation process. In some embodiments, the formulations described above are lyophilized, i.e., they are subjected to lyophilization. In some embodiments, the formulations described above are subjected to a preservation process, for example, lyophilization, and are subsequently reconstituted with a suitable liquid, for example, water. By lyophilized it is meant that the composition has been freeze-dried under a vacuum. Lyophilization typically is accomplished by freezing a particular formulation such that the solutes are separated from the solvent(s). The solvent is then removed by sublimation (i.e., primary drying) and next by desorption (i.e., secondary drying).

In some embodiments, lyophilized formulations of the present invention comprise the antibody-drug conjugate, a buffering agent, optionally a cryoprotectant, optionally a bulking agent, optionally a salt, and optionally a surfactant as well as additional agents, wherein the composition has a pH of about 5.3-7 when reconstituted with water. In some embodiments, lyophilized formulations of the present invention, when reconstituted with water, comprise (i) about 1-25 mg/ml, preferably about 3 to about 10 mg/ml, of an antibody-drug conjugate (e.g., an antibody-drug conjugate of formula I or a pharmaceutically acceptable salt thereof), (ii) about 5-50 mM, preferably about 10 mM to about 25 mM of a buffer selected from a citrate, phosphate, or histidine buffer or combinations thereof, preferably sodium citrate, potassium phosphate, histidine, histidine hydrochloride, or combinations thereof, (iii) about 3% to about 10% sucrose or trehalose or combinations thereof, and (iv) optionally about 0.05 to 2 mg/ml of a surfactant selected from polysorbate 20 or polysorbate 80 or combinations thereof; wherein the pH of the composition is from about 5.3 to about 7, preferably about 6.6.

In some embodiments, lyophilized formulations, when reconstituted with water, comprise (i) about 1-25 mg/ml, preferably about 3 to about 10 mg/ml, even more preferably about 5 mg/ml of an antibody-drug conjugate (ii) about 10 mM to about 25 mM of a buffer selected from sodium citrate, potassium phosphate, histidine, histidine hydrochloride or combinations thereof, (iii) about 3% to about 7% trehalose or sucrose or combinations thereof, and optionally (iv) about 0.05 to about 1 mg/ml of a surfactant selected from polysorbate 20 or polysorbate 80, wherein the pH of the composition is from about 5.3 to about 7, preferably about 6.6.

In some embodiments, lyophilized formulations, when reconstituted with water, comprise about 5 mg/ml of an antibody-drug conjugate of the present invention, (ii) about 10 mM to about 25 mM of a buffer selected from sodium citrate, potassium phosphate, histidine, histidine hydrochloride, or combinations thereof, (iii) about 3% to about 7% trehalose, optionally (iv) about 0.05 to about 1 mg/ml of a surfactant selected from polysorbate 20 or polysorbate 80, wherein the pH of the composition is from about 5.3 to about 7, preferably about 6.6.

In some embodiments, lyophilized formulations, when reconstituted with water, comprise (or consist essentially of) about 5 mg/ml of an antibody-drug conjugate of the present invention, (ii) about 20 mM sodium citrate (iii) about 6% to about 7% trehalose (about 70 mg/ml), (iv) about 0.1 to 0.3 mg/ml of a surfactant selected from polysorbate 20 or polysorbate 80 (preferably polysorbate 80) wherein the pH of the composition is from about 5.3 to about 7, preferably about 6.6.

The formulations of the present invention can be used with the methods described herein or with other methods for treating disease. The antibody drug conjugate formulations may be further diluted before administration to a subject. In some embodiments, the formulations will be diluted with saline and held in IV bags or syringes before administration to a subject. Accordingly, in some embodiments, the methods for treating a CD30-expressing hematologic cancer in a subject will comprise administering to a subject in need thereof a weekly dose of a pharmaceutical composition comprising antibody-drug conjugates having formula I wherein the administered dose of antibody-drug conjugates is from about 0.8 mg/kg of the subject's body weight to about 1.8 mg/kg of the subject's body weight and the pharmaceutical composition is administered for at least three weeks and wherein the antibody drug conjugates, prior to administration to a subject, were present in a formulation comprising (i) about 1-25 mg/ml, preferably about 3 to about 10 mg/ml of the antibody-drug conjugate (ii) about 5-50 mM, preferably about 10 mM to about 25 mM of a buffer selected from sodium citrate, potassium phosphate, histidine, histidine hydrochloride, or combinations thereof, (iii) about 3% to about 10% sucrose or trehalose or combinations thereof, (iv) optionally about 0.05 to 2 mg/ml of a surfactant selected from polysorbate 20 or polysorbate 80 or combinations thereof; and (v) water, wherein the pH of the composition is from about 5.3 to about 7, preferably about 6.6.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed, for example, with an infusion bottle containing sterile pharmaceutical grade water or saline. Where the pharmaceutical is administered by injection, an ampoule of sterile water for injection or saline can be, for example, provided so that the ingredients can be mixed prior to administration.

The present invention also provides kits for the treatment of a CD30-expressing hematologic cancer. The kit can comprise (a) a container containing the antibody-drug conjugate. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

All publications and patent documents cited above are hereby incorporated by reference in their entirety for all purposes to the same extent as if each were so individually denoted.

The invention is further described in the following examples, which are in not intended to limit the scope of the invention.

EXAMPLES

A multicenter, phase 1, weekly dosing, dose escalation study was conducted in pts with refractory or relapsed HL or systemic ALCL. The cAC10-MC-vc-PAB-MMAE antibody drug conjugate was administered weekly at doses of 0.4-1.4 mg/kg (2-hr IV infusions). Patients with standard disease or better after two 21-day cycles (6 doses) were eligible to continue treatment with the antibody drug conjugate. The weekly study design is provided in FIG. 1.

Results:

In 34 patients, median age was 34 yrs (range 13-82). Patients received a median of 5 prior therapies; 62% received an autologous SCT. MTD was exceeded at 1.4 mg/kg. Exposure to SGN-35 (AUC) increased relative to dose level. Multiple CRs were observed at higher doses (table); observed time to response for 1 mg/kg dose was approximately 8 wks.

TABLE 2

Best Clinical Response*

| Dose Group (mg/kg) | N | CR | PR | SD | PD |
|---|---|---|---|---|---|
| 0.4 | 4 | — | — | 4+ | — |
| 0.6 | 3 | — | 1 | 1 | 1 |
| 0.8 | 6 | 4++ | — | 1$^P$ | 1 |
| 1.0 | 6 | 4++ | 1 | 1 | — |
| 1.2 | 5 | — | 1 | 3$^P$ | 1 |
| 1.4 | 3 | 2 | — | 1 | — |
| Total | 27 | 10 | 3 | 22 | 3 |

*Based on International Working Group Revised Response Criteria for Malignant Lymphoma (Cheson, 2007). 7 patients not evaluable (pending Cycle 2 restage).
+represents 1 patient with ALCL;
++represents 2 patient with ALCL;
each P represents 1 pediatric patient (12-17 years)

TABLE 3

| Response Rate | Percent Response | | |
|---|---|---|---|
| | All Patients | HL Patients | sALCL patients |
| Overall Response Rate (CR + PR) | 48% (13/27) | 41% (9/22) | 80% (4/5) |
| Complete Response | 37% (10/27) | 27% (6/22) | 80% (4/5) |
| Tumor Reductions | 81% (22/27) | | |

The cAC10-MC-vc-PAB-MMAE antibody drug conjugate was generally well tolerated in the 34 treated patients. There were no grade 5 events. The grade 4 events were neutropenia (1 subject), and hyperglycemia (1). The grade 3 events were neutropenia (3), diarrhea (1), paresthesia (1), vomiting (1), and leucopenia (1). The grade 2 or lower adverse events were nausea (9), fatigue (8), peripheral neuropathy (6), neutropenia (2), dizziness (4), hyperglycemia (3), and paresthesia (3). The dose limiting toxicity was at 1.4 mg/kg.

```
                     SEQUENCE LISTING

SEQ ID NO: 1
cag atc cag ctg cag cag tct gga cct gag gtg gtg aag cct ggg gct
tca gtg aag ata tcc tgc aag gct tct ggc tac acc ttc act gac tac
tat ata acc tgg gtg aag cag aag cct gga ctt gag tgg att
gga tgg att tat cct gga agc ggt aat act aag tac aat gag aag ttc
aag ggc aag gcc aca ttg act gta gac aca tcc tcc agc aca gcc ttc
atg cag ctc agc agc ctg aca tct gag gac act gct gtc tat ttc tgt
gcg aac tat ggt aac tac tgg ttt gct tac tgg ggc caa ggg act cag
gtc act gtc tct gca SEQ ID NO: 2
Gln Ile Gln Leu Gln Gln Ser Gly Pro Glu Val Val Lys Pro Gly Ala
Ser Val Lys Ile Ser Cys Lys Ala Ser Gly Tyr Thr Phe Thr Asp Tyr
Tyr Ile Thr Trp Val Lys Gln Lys Pro Gly Gln Gly Leu Glu Trp Ile
Gly Trp Ile Tyr Pro Gly Ser Gly Asn Thr Lys Tyr Asn Glu Lys Phe
Lys Gly Lys Ala Thr Leu Thr Val Asp Thr Ser Ser Ser Thr Ala Phe
Met Gln Leu Ser Ser Leu Thr Ser Glu Asp Thr Ala Val Tyr Phe Cys
Ala Asn Tyr Gly Asn Tyr Trp Phe Ala Tyr Trp Gly Gln Gly Thr Gln
Val Thr Val Ser Ala SEQ ID NO: 3
gactactata taacc SEQ ID NO: 4
Asp Tyr Tyr Ile Thr SEQ ID NO: 5
tggatttatc ctggaagcgg taatactaag tacaatgaga agttcaaggg c SEQ ID NO: 6
Trp Ile Tyr Pro Gly Ser Gly Asn Thr Lys Tyr Asn Glu Lys Phe Lys
Gly SEQ ID NO: 7
tatggtaact actggtttgc ttac 24

SEQ ID NO: 8
Tyr Gly Asn Tyr Trp Phe Ala Tyr

SEQ ID NO: 9
gac att gtg ctg acc caa tct cca gct tct ttg gct gtg tct cta ggg
cag agg gcc acc atc tcc tgc aag gcc agc caa agt gtt gat ttt gat
ggt gat agt tat atg aac tgg tac caa cag aaa cca gga cag cca ccc
aaa gtc ctc atc tat gct gca tcc aat cta gaa tct ggg atc cca gcc
agg ttt agt ggc agt ggg tct ggg aca gac ttc acc ctc aac atc cat
cct gtg gag gag gag gat gct gca acc tat tac tgt cag caa agt aat
gag gat ccg tgg acg ttc ggt gga ggc acc aag ctg gaa atc aaa SEQ ID NO: 10
Asp Ile Val Leu Thr Gln Ser Pro Ala Ser Leu Ala Val Ser Leu Gly
Gln Arg Ala Thr Ile Ser Cys Lys Ala Ser Gln Ser Val Asp Phe Asp
Gly Asp Ser Tyr Met Asn Trp Tyr Gln Gln Lys Pro Gly Gln Pro Pro
Lys Val Leu Ile Tyr Ala Ala Ser Asn Leu Glu Ser Gly Ile Pro Ala
Arg Phe Ser Gly Ser Gly Ser Gly Thr Asp Phe Thr Leu Asn Ile His
Pro Val Glu Glu Glu Asp Ala Ala Thr Tyr Tyr Cys Gln Gln Ser Asn
Glu Asp Pro Trp Thr Phe Gly Gly Gly Thr Lys Leu Glu Ile Lys SEQ ID NO: 11
aaggccagcc aaagtgttga ttttgatggt gatagttata tgaac SEQ ID NO: 12
Lys Ala Ser Gln Ser Val Asp Phe Asp Gly Asp Ser Tyr Met Asn SEQ ID NO: 13
gctgcatcca atctagaatc t
```

-continued

SEQUENCE LISTING

SEQ ID NO: 14
Ala Ala Ser Asn Leu Glu Ser

SEQ ID NO: 15
cagcaaagta atgaggatcc gtggacg

SEQ ID NO: 16
Gln Gln Ser Asn Glu Asp Pro Trp Thr

SEQ ID NO: 17
gag gtg aag ctg gtg gag tct gga gga ggc ttg gta cag cct ggg ggt
tct ctg aga ctc tcc tgt gca act tct ggg ttc acc ttc agt gat tac
tat atg aac tgg gtc cgc cag cct cca gga aag gct ctt gag tgg ttg
ggt ttt att aga aac aaa gct aat ggt tac aca aca gag ttc agt gca
tct gtg atg ggt cgg ttc acc atc tcc aga gat gat tcc caa agc atc
ctc tat ctt cag atg aac acc ctg aga gct gag gac agt gcc act tat
tac tgt gca aga gat ccc ccc tat ggt aac ccc cat tat tat gct atg
gac tac tgg ggt caa gga acc tca gtc acc gtc tcc tca SEQ ID NO: 18
Glu Val Lys Leu Val Glu Ser Gly Gly Gly Leu Val Gln Pro Gly Gly
Ser Leu Arg Leu Ser Cys Ala Thr Ser Gly Phe Thr Phe Ser Asp Tyr
Tyr Met Asn Trp Val Arg Gln Pro Pro Gly Lys Ala Leu Glu Trp Leu
Gly Phe Ile Arg Asn Lys Ala Asn Gly Tyr Thr Thr Glu Phe Ser Ala
Ser Val Met Gly Arg Phe Thr Ile Ser Arg Asp Asp Ser Gln Ser Ile
Leu Tyr Leu Gln Met Asn Thr Leu Arg Ala Glu Asp Ser Ala Thr Tyr
Tyr Cys Ala Arg Asp Pro Pro Tyr Gly Asn Pro His Tyr Tyr Ala Met
Asp Tyr Trp Gly Gln Gly Thr Ser Val Thr Val Ser Ser SEQ ID NO: 19
gattactata tgaac SEQ ID NO: 20
Asp Tyr Tyr Met Asn SEQ ID NO: 21
tttattagaa acaaagctaa tggttacaca acagagttca gtgcatctgt gatgggt SEQ ID NO: 22
Phe Ile Arg Asn Lys Ala Asn Gly Tyr Thr Thr Glu Phe Ser Ala Ser
Val Met Gly SEQ ID NO: 23
gatccccct atggtaaccc ccattattat gctatggact ac SEQ ID NO: 24
Asp Pro Pro Tyr Gly Asn Pro His Tyr Tyr Ala Met Asp Tyr SEQ ID NO: 25
gac att gtg ctg acc cag tct cct gct tcc tta gct gtt tct ctg ggg
cag agg gcc acc atc tca tgc agg gcc agc aaa agt gtc agt gca tct
ggc tat aat tat atg cac tgg tac caa cag aaa gca ggg cag cca ccc
aaa ctc ctc atc cat ctt gca tcc aac cta gaa tct ggg gtc cct gcc
agg ttc agt ggc agt ggg tct ggg aca gac ttc acc ctc aac atc cat
cct gtg gag gag gag gat gct tca acc tat tac tgt cag cac agt ggg
gag ctt cca ttc acg ttc ggc tcg ggg aca aag ttg gaa ata aaa SEQ ID NO: 26
Asp Ile Val Leu Thr Gln Ser Pro Ala Ser Leu Ala Val Ser Leu Gly
Gln Arg Ala Thr Ile Ser Cys Arg Ala Ser Lys Ser Val Ser Ala Ser
Gly Tyr Asn Tyr Met His Trp Tyr Gln Gln Lys Ala Gly Gln Pro Pro
Lys Leu Leu Ile His Leu Ala Ser Asn Leu Glu Ser Gly Val Pro Ala
Arg Phe Ser Gly Ser Gly Ser Gly Thr Asp Phe Thr Leu Asn Ile His
Pro Val Glu Glu Glu Asp Ala Ser Thr Tyr Tyr Cys Gln His Ser Gly
Glu Leu Pro Phe Thr Phe Gly Ser Gly Thr Lys Leu Glu Ile Lys SEQ ID NO: 27
agggccagca aaagtgtcag tgcatctggc tataattata tgcac SEQ ID NO: 28
Arg Ala Ser Lys Ser Val Ser Ala Ser Gly Tyr Asn Tyr Met His SEQ ID NO: 29
cttgcatcca acctagaatc t

SEQUENCE LISTING

SEQ ID NO: 30
Leu Ala Ser Asn Leu Glu Ser

SEQ ID NO: 31
cagcacagtg gggagcttcc atteacg

SEQ ID NO: 32
Gln His Ser Gly Glu Leu Pro Phe Thr

SEQ ID NO: 33
Ala Ser Thr Lys Gly Pro Ser Val Phe Pro Leu Ala Pro Ser Ser Lys
Ser Thr Ser Gly Gly Thr Ala Ala Leu Gly Cys Leu Val Lys Asp Tyr
Phe Pro Glu Pro Val Thr Val Ser Trp Asn Ser Gly Ala Leu Thr Ser
Gly Val His Thr Phe Pro Ala Val Leu Gln Ser Ser Gly Leu Tyr Ser
Leu Ser Ser Val Val Thr Val Pro Ser Ser Ser Leu Gly Thr Gln Thr
Tyr Ile Cys Asn Val Asn His Lys Pro Ser Asn Thr Lys Val Asp Lys
Lys Val Glu Pro Lys Ser Cys Asp Lys Thr His Thr Cys Pro Pro Cys
Pro Ala Pro Glu Leu Leu Gly Gly Pro Ser Val Phe Leu Phe Pro Pro
Lys Pro Lys Asp Thr Leu Met Ile Ser Arg Thr Pro Glu Val Thr Cys
Val Val Val Asp Val Ser His Glu Asp Pro Glu Val Lys Phe Asn Trp
Tyr Val Asp Gly Val Glu Val His Asn Ala Lys Thr Lys Pro Arg Glu
Glu Gln Tyr Asn Ser Thr Tyr Arg Val Val Ser Val Lou Thr Val Lou
His Gln Asp Trp Leu Asn Gly Lys Glu Tyr Lys Cys Lys Val Ser Asn
Lys Ala Lou Pro Ala Pro Ile Glu Lys Thr Ile Ser Lys Ala Lys Gly
Gln Pro Arg Glu Pro Gln Val Tyr Thr Leu Pro Pro Ser Arg Asp Glu
Leu Thr Lys Asn Gln Val Ser Leu Thr Cys Leu Val Lys Gly Phe Tyr
Pro Ser Asp Ile Ala Val Glu Trp Glu Ser Asn Gly Gln Pro Glu Asn
Asn Tyr Lys Thr Thr Pro Pro Val Leu Asp Ser Asp Gly Ser Phe Phe
Leu Tyr Ser Lys Leu Thr Val Asp Lys Ser Arg Trp Gln Gln Gly Asn
Val Phe Ser Cys Ser Val Met His Glu Ala Leu His Asn His Tyr Thr
Gln Lys Ser Leu Ser Leu Ser Pro Gly Lys

SEQ ID NO: 34
Thr Val Ala Ala Pro Ser Val Phe Ile Phe Pro Pro Ser Asp Glu Gln
Leu Lys Ser Gly Thr Ala Ser Val Val Cys Leu Leu Asn Asn Phe Tyr
Pro Arg Glu Ala Lys Val Gln Trp Lys Val Asp Asn Ala Leu Gln Ser
Gly Asn Ser Gln Glu Ser Val Thr Glu Gln Asp Ser Lys Asp Ser Thr
Tyr Ser Leu Ser Ser Thr Leu Thr Leu Ser Lys Ala Asp Tyr Glu Lys
His Lys Val Tyr Ala Cys Glu Val Thr His Gln Gly Leu Ser Ser Pro
Val Thr Lys Ser Phe Asn Arg Gly Glu Cys

What is claimed is:

1. A method for treating a CD30-expressing hematologic cancer in a human subject, the method comprising administering to a human subject in need thereof a dose of a pharmaceutical composition comprising (i) cAC10-MC-vc-PAB-MMAE antibody-drug conjugate, and (ii) a pharmaceutically acceptable carrier, wherein the administered dose of cAC10-MC-vc-PAB-MMAE antibody-drug conjugate is 1.8 mg/kg of the human subject's body weight and the pharmaceutical composition is administered every three weeks, wherein the pharmaceutical composition is administered by intravenous infusion to the human subject.

2. The method of claim 1, wherein the average number of MMAE molecules per cAC10 antibody of the cAC10-MC-vc-PAB-MMAE antibody-drug conjugate in the pharmaceutical composition is about 4.

3. The method of claim 1, wherein the CD30-expressing hematologic cancer is Hodgkin Lymphoma.

4. The method of claim 3, wherein the average number of MMAE molecules per cAC10 antibody of the cAC10-MC-vc-PAB-MMAE antibody-drug conjugate in the pharmaceutical composition is about 4.

5. The method of claim 1, wherein the CD30-expressing hematologic cancer is anaplastic large cell lymphoma.

6. The method of claim 5, wherein the average number of MMAE molecules per cAC10 antibody of the cAC10-MC-vc-PAB-MMAE antibody-drug conjugate in the pharmaceutical composition is about 4.

7. The method of claim 1, wherein the human subject has not previously been treated for the CD30-expressing hematologic cancer.

8. The method of claim 3, wherein the human subject has not previously been treated for the CD30-expressing hematologic cancer.

9. The method of claim 1, wherein the human subject has been previously treated with one or more anti-cancer therapies and relapsed after the treatment.

10. The method of claim 9, wherein the one or more anti-cancer therapies was a first-line chemotherapy regimen and/or a salvage regimen and/or an experimental treatment for the CD30-expressing hematologic cancer.

11. The method of claim 3, wherein the human subject has been previously treated with one or more anti-cancer therapies and relapsed after the treatment.

12. The method of claim 5, wherein the human subject has been previously treated with one or more anti-cancer therapies and relapsed after the treatment.

13. The method of claim 1, wherein the human subject has been previously treated with one or more anti-cancer therapies and has experienced disease progression during treatment.

14. The method of claim 13, wherein the one or more anti-cancer therapies was a first-line chemotherapy regimen and/or a salvage regimen and/or an experimental treatment for the CD30-expressing hematologic cancer.

15. The method of claim 3, wherein the human subject has been previously treated with one or more anti-cancer therapies and has experienced disease progression during treatment.

16. The method of claim 5, wherein the human subject has been previously treated with one or more anti-cancer therapies and has experienced disease progression during treatment.

17. The method of claim 1, wherein the subject has previously undergone a stem cell transplant for treatment of the CD30-expressing hematologic cancer.

18. The method of claim 17, wherein the human subject has no detectable sign of the CD30-expressing hematologic cancer.

19. The method of claim 17, wherein the human subject relapsed after the stem cell transplant.

20. The method of claim 3, wherein the human subject has previously undergone a stem cell transplant for treatment of the CD30-expressing hematologic cancer.

21. The method of claim 5, wherein the human subject has previously undergone a stem cell transplant for treatment of the CD30-expressing hematologic cancer.

22. The method of claim 1, wherein the cAC10-MC-vc-PAB-MMAE antibody-drug conjugate has undergone lyophilization.

23. The method of claim 1, further comprising administering an anti-inflammatory agent to the human subject.

* * * * *